United States Patent
Iniewski et al.

(10) Patent No.: US 11,246,547 B2
(45) Date of Patent: Feb. 15, 2022

(54) COMPENSATION FOR CHARGE SHARING BETWEEN DETECTOR PIXELS IN A PIXILATED RADIATION DETECTOR

(71) Applicant: REDLEN TECHNOLOGIES, INC., Saanichton (CA)

(72) Inventors: Krzysztof Iniewski, Coquitlam (CA); Elmaddin Guliyev, Vancouver (CA); Conny Hansson, Victoria (CA)

(73) Assignee: REDLEN TECHNOLOGIES, INC., Saanichton (CA)

(*) Notice: Subject to any disclaimer, the term of this patent is extended or adjusted under 35 U.S.C. 154(b) by 0 days.

(21) Appl. No.: 16/931,800

(22) Filed: Jul. 17, 2020

(65) Prior Publication Data

US 2021/0022695 A1 Jan. 28, 2021

Related U.S. Application Data

(60) Provisional application No. 62/877,231, filed on Jul. 22, 2019.

(51) Int. Cl.
*A61B 6/00* (2006.01)
*A61B 6/03* (2006.01)

(52) U.S. Cl.
CPC .......... *A61B 6/4241* (2013.01); *A61B 6/037* (2013.01); *A61B 6/485* (2013.01); *A61B 6/5217* (2013.01); *A61B 6/58* (2013.01)

(58) Field of Classification Search
CPC ....... A61B 6/4241; A61B 6/5217; A61B 6/58; A61B 6/485; A61B 6/037; A61B 6/4035;
(Continued)

(56) References Cited

U.S. PATENT DOCUMENTS 7,208,739 B1 * 4/2007 Yanoff .............. G01T 1/171
250/363.09
10,151,845 B1 * 12/2018 Viswanath .......... G01T 1/17
(Continued)

OTHER PUBLICATIONS

U.S. Appl. No. 16/844,484, filed Apr. 9, 2020, Redlen Technologies, Inc.
(Continued)

*Primary Examiner* — Marcus H Taningco
(74) *Attorney, Agent, or Firm* — The Marbury Law Group PLLC

(57) ABSTRACT

Various aspects include methods for compensating for the effects of charge sharing among pixelate detectors in X-ray detectors by applying a correspondence factor to counts of X-ray photons in energy bins to estimate incident X-ray photon energy bins. The correspondence factor may be determined by determining an incident X-ray photon energy spectrum, adjusting the incident X-ray photon energy spectrum to account for an energy resolution of the pixelated detector, generating a charge sharing model for the adjusted incident X-ray photon energy spectrum based on a percentage charge sharing parameter of the pixelated detector, applying the charge sharing model to energy bins of the pixelated detector to estimate counts in each of the energy bins, and determining the correspondence factor by comparing the estimated counts in each of the energy bins to counts in the energy bins that would be expected for the adjusting the incident X-ray photon energy spectrum.

10 Claims, 21 Drawing Sheets

(58) Field of Classification Search
CPC ....... A61B 6/4042; A61B 6/482; A61B 6/025; G01T 1/36
See application file for complete search history.

(56) References Cited

U.S. PATENT DOCUMENTS

| | | | |
|---|---|---|---|
| 10,365,380 B2* | 7/2019 | Steadman Booker | G01T 1/17 |
| 10,393,891 B2 | 8/2019 | Iniewski et al. | |
| 10,396,109 B2 | 8/2019 | Iniewski et al. | |
| 10,677,942 B2* | 6/2020 | Cao | G01T 1/24 |
| 2008/0175347 A1* | 7/2008 | Tkaczyk | G01T 1/24 |
| | | | 378/7 |
| 2012/0112088 A1* | 5/2012 | Abraham | G01T 1/171 |
| | | | 250/395 |
| 2017/0020475 A1* | 1/2017 | Spahn | H04N 5/21 |
| 2017/0290555 A1 | 10/2017 | Iniewski et al. | |
| 2017/0322319 A1 | 11/2017 | Iniewski et al. | |
| 2018/0329086 A1* | 11/2018 | Roessl | G01T 1/2928 |
| 2020/0150297 A1 | 5/2020 | Iniewski et al. | |

OTHER PUBLICATIONS

U.S. Appl. No. 16/875,133, filed May 15, 2020, Redlen Technologies, Inc.
U.S. Appl. No. 16/894,063, filed Jun. 5, 2020, Redlen Technologies, Inc.

* cited by examiner

COMPENSATION FOR CHARGE SHARING BETWEEN DETECTOR PIXELS IN A PIXILATED RADIATION DETECTOR

FIELD

The present application relates generally to radiation detectors for X-ray imaging systems.

BACKGROUND

In typical photon counting X-ray applications currently in use, the charge cloud resulting from an X-ray photon impinging on a sensor is converted to an amplified voltage by a charge sensitive amplifier (CSA). The voltage output of the CSA is compared against a number of user-settable thresholds. Each threshold level is associated with a counter that increments when the voltage output falls between the minimum and maximum thresholds associated with the counter. Thus, each counter records the number of photons detected within the energy range between two adjacent thresholds, which is referred to as an energy bin.

The lowest threshold is set to slightly above the noise level, and a voltage above this threshold indicates that an X-ray photon has been detected. After the CSA output voltage has stabilized, the counter corresponding to the highest energy bin threshold crossed is incremented, thus recording one detection event in that energy bin. As the count is registered in an energy bin, the CSA is reset, enabling the detector pixel to record another X-ray detection event. If the X-ray photon is absorbed near the center of a pixel detector, this process yields an accurate count of photon energies. However, if the X-ray photon is absorbed near the boundary of a pixel detector or within the gap between two or more pixel detectors, the charge cloud produced by the photon absorption may be shared between two or more pixel detectors, resulting in an inaccurate count of photon energies due to charge sharing.

SUMMARY

Various aspects may include X-ray photon detectors and methods of operating such detectors that compensate for charge sharing effects. In particular, various aspects include methods of accounting for difference between observed energies X-ray photons and an incident X-ray photon energy spectrum that accounts for charge sharing in a pixelated detector within an X-ray imaging system. Various aspects may include applying a correspondence factor to counts of X-ray photons in energy bins to estimate incident X-ray photon energy bins, wherein the correspondence factor accounts for charge sharing within the pixelated detector. Various aspects may further include determining the correspondence factor by determining a photon energy spectrum of X-ray photons incident on the pixelated detector ("incident X-ray photon energy spectrum") adjusting the incident X-ray photon energy spectrum to account for an energy resolution of the pixelated detector, generating a charge sharing model for the adjusted incident X-ray photon energy spectrum based on a percentage charge sharing parameter of the pixelated detector, the charge sharing model accounting for shifts in photon energies and detections occurring in photon detections due to charge sharing in the pixelated detector, applying the charge sharing model to energy bins of the pixelated detector to estimate counts in each of the energy bins, and determining the correspondence factor by comparing the estimated counts in each of the energy bins to counts in the energy bins that would be expected for the adjusting the incident X-ray photon energy spectrum.

In some aspects, determining the incident X-ray photon energy spectrum may include obtaining an X-ray photon energy spectrum emitted from an X-ray tube of the imaging system, adjusting the emitted X-ray photon energy spectrum by a factor accounting for X-ray photon absorption properties of the pixelated detector, and further adjusting the X-ray photon energy spectrum to account for hardening of the spectrum due to effects of one or both of a filter in the X-ray imaging system or of an object under examination in the X-ray imaging system.

Some aspects may further include determining the energy resolution of the pixelated detector by measuring, with the pixelated detector, X-ray photon energies emitted by an isotope with a characteristic X-ray emission of a specific energy, and determining a range of measured energies having at least a count rate equal to half of a maximum count rate at a measured energy peak corresponding to the specific energy of the characteristic X-ray emission of the isotope. Some aspects may further include determining the percentage of charge sharing parameter of the pixelated detector by using the pixelated detector to measure X-ray photon energies emitted by an isotope with a specific energy X-ray emission, and determining a fraction of photon detection counts with energies less than the specific energy X-ray emission plus half of the energy resolution to all photon detection counts including counts about the specific energy of the isotope characteristic X-ray emission.

Some aspects may further include adjusting the charge sharing model to address X-ray fluorescence effects. Some aspects may further include adjusting the charge sharing model to address pile-up effects.

Some aspects may further include selecting a number of energy bins, and repeating operations of applying the charge sharing model to the selected energy bins and determining the correspondence factor until a full correspondence is established between counted photons in the selected energy bins and counts in the energy bins that would be expected for the adjusting the incident X-ray photon energy spectrum.

In some aspects, generating a charge sharing model for the adjusted incident X-ray photon energy spectrum based on a percentage charge sharing parameter of the pixelated detector may include, for the full the adjusted incident X-ray photon energy spectrum, spreading count rates of narrow slices of the adjusted incident X-ray photon spectrum across energies from zero to the energy of each narrow slice, and summing all spread count rates to determine an X-ray photon energy spectrum that would be observed by the pixelated detector due to charge sharing before segmenting the spectrum into energy bins.

Further aspects include a computing device for use in an X-ray imaging system configured with processor-executable instructions to perform operations of any of the methods summarized above. Further aspects include a processor-readable storage medium having stored thereon processor-executable instructions configured to cause a computing device in an X-ray imaging system with to perform operations of any of the methods summarized above.

BRIEF DESCRIPTION OF THE DRAWINGS

The accompanying drawings are presented to aid in the description of embodiments of the disclosure and are provided solely for illustration of the embodiments and not limitation thereof.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims. Any reference to claim elements in the singular, for example, using the articles "a," "an," or "the" is not to be construed as limiting the element to the singular. The terms "example," "exemplary," or any term of the like are used herein to mean serving as an example, instance, or illustration. Any implementation described herein as an "example" is not necessarily to be construed as preferred or advantageous over another implementation. The drawings are not drawn to scale. Multiple instances of an element may be duplicated where a single instance of the element is illustrated, unless absence of duplication of elements is expressly described or clearly indicated otherwise.

Various embodiments improve on imaging X-ray detectors by compensating for the effects of charge sharing in a pixelated detector. In various embodiments, the energy resolution and the percentage of charge sharing (PCS) characteristics of a pixelated detector are determined. Using these parameters and an X-ray spectrum determined through simulation, effects of detector absorption, spectrum hardening from filter or target absorption, and other effects are taken into account before a charge sharing algorithm is used to determine the number of photons in each energy bin resulting from charge sharing. The process may be repeated as require to establish a full correlation between measured X-ray spectrum in finite energy bins after charge sharing and the energy of X-ray photons before charge sharing effects. Using the results of this correlation, an estimate of the actual X-ray spectrum before charge sharing effects can be estimated based on the X-ray spectrum measured by a pixelated detector.

Figure 1A:
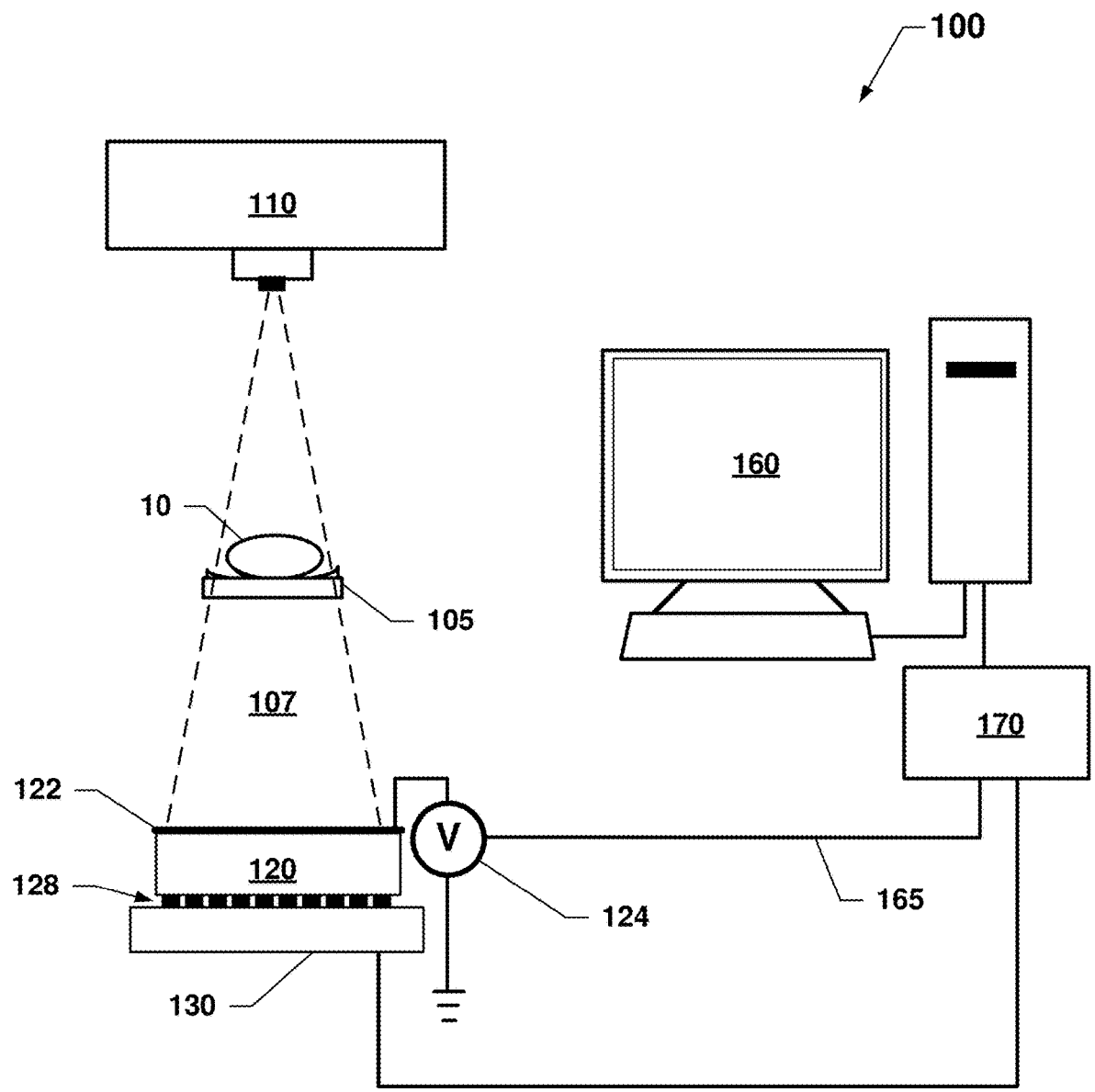
FIG. 1A is a block diagram of an X-ray imaging system suitable for use with various embodiments of the present disclosure.

FIG. 1A is a functional block diagram of an X-ray imaging system 100 in accordance with various embodiments. The X-ray imaging system 100 may include an X-ray source 110 (i.e., a source of ionizing radiation), and a radiation detector 120. The X-ray imaging system 100 may additionally include a support structure 105, such as a table or frame, which may rest on the floor and may support an object 10 to be scanned. The support structure 105 may be stationary (i.e., non-moving) or may be configured to move relative to other elements of the X-ray imaging system 100. The object 10 may be a component or material that is the subject of non-destructive testing (NDT), a biological (e.g., human patient) object, or an inanimate object (e.g., luggage) to be scanned.

The X-ray source 110 is configured to deliver ionizing radiation to the radiation detector 120 by emitting an X-ray beam 107 toward the object 10 and the radiation detector 120. After the X-ray beam 107 is attenuated by the object 10, the beam of radiation 107 is received by the radiation detector 120.

The radiation detector 120 may be controlled by a high voltage bias power supply 124 that selectively creates an electric field between an anode 122 and cathode 128 pair coupled thereto. The radiation detector 120 may include CdZnTe (CZT) material disposed between the anode 122 and cathode 128 and thus configured to be exposed to the electrical field therebetween. A read-out application specific integrated circuit (ASIC) 130 coupled to the anode 122 and cathode 128 pair may receive signals (e.g., charge or current) from the anode 122 and be configured to provide data to and by controlled by a control unit 170. The radiation detector 120 may be segmented or configured into a large number of small "pixel" detectors. In various embodiments, the radiation detector 120 pixel detectors and the ASIC 130 are configured to output data that includes counts of photons detected in each pixel detector in each of a number of energy bins. Thus, energy detectors 120 of various embodiments provide both two-dimensional detection information regarding where photons were detected, thereby providing image information, and measurements of the X-ray energy of the detected photons.

The control unit 170 may be configured to synchronize the X-ray source 110, the read-out ASIC 130, and the high voltage bias power supply 124. The control unit 170 may be coupled to and operated from a computing device 160. Alternatively, the computing device 160 and the control unit 170 may be integrated together as one device.

The object 10 may slowly pass between the X-ray source 110 and the radiation detector 120 or alternatively the object may remain stationary while the X-ray source 110 and the radiation detector 120 move relative to the object 10. Either way, the radiation detector 120 may capture incremental cross-sectional profiles of the object 10. The data acquired by the radiation detector 120 may be passed along to the computing device 160 that may be located remotely from the radiation detector 120 via a connection 165. The connection 165 may be any type of wired or wireless connection. If the connection 165 is a wired connection, the connection 165 may include a slip ring electrical connection between any structure supporting the radiation detector 120 and a stationary support part of the support structure 105, which supports any part (e.g., a rotating ring). If the connection 165 is a wireless connection, the radiation detector 120 may contain any suitable wireless transceiver to communicate data with another wireless transceiver that is in communication with the computing device 160. The computing device 160 may include processing and imaging applications that analyze each profile obtained by the radiation detector 120, and a full set of profiles may be compiled to form two-dimensional images of cross-sectional slices of the object 10.

Various alternatives to the design of the X-ray imaging system 100 of FIG. 1 may be employed to practice embodiments of the present disclosure. X-ray imaging systems may be designed in various architectures and configurations. For example, an X-ray imaging system may have a helical architecture. In a helical X-ray imaging scanner, the X-ray source and detector array are attached to a freely rotating gantry. During a scan, a table moves the object smoothly through the scanner creating helical path traced out by the X-ray beam. Slip rings enable the transfer of power and data on and off the rotating gantry. In other embodiments, the X-ray imaging system may be a tomosynthesis X-ray imaging system. In a tomosynthesis X-ray scanner, the gantry may move in a limited rotation angle (e.g., between 15 degrees and 60 degrees) in order to detect a cross-sectional slice of the object. The tomosynthesis X-ray scanner may be able to acquire slices at different depths and with different thicknesses that may be constructed via image processing.

Figure 1B:
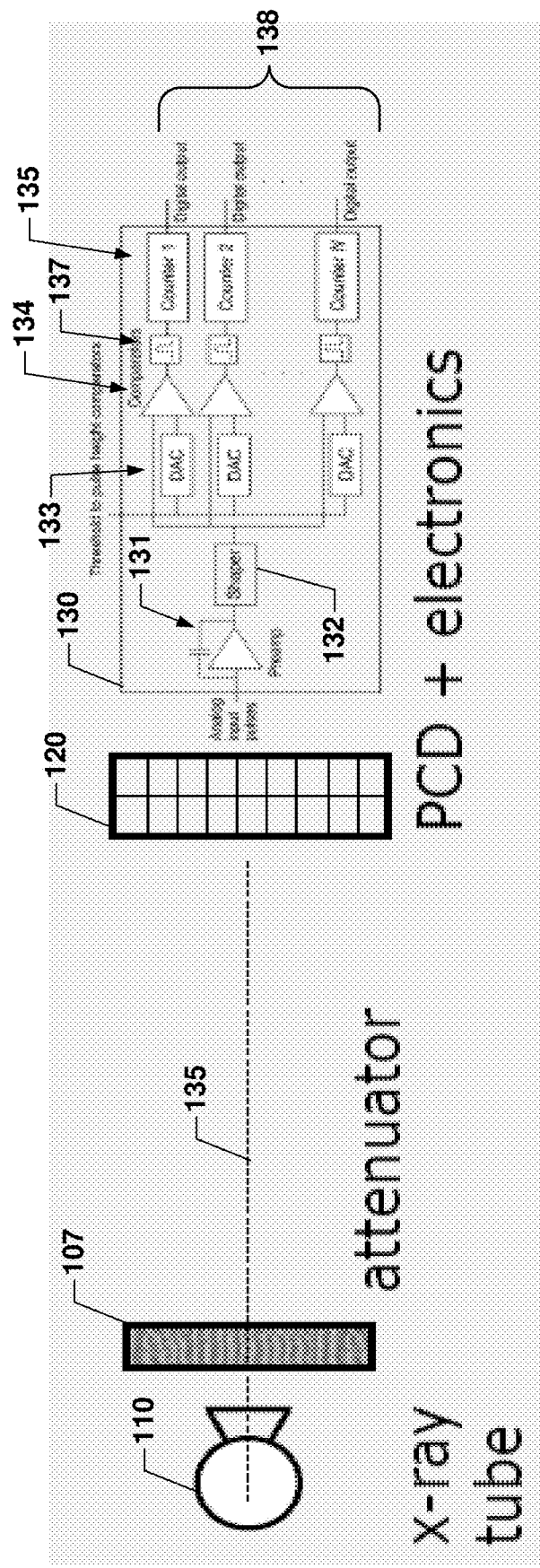
FIG. 1B is a block diagram illustrating components of an X-ray imaging system

FIG. 1B illustrates components of an X-ray imaging system, including components within the ASIC 130 configured to count X-ray photons detected in each pixel detector within a set of energy bins. As used herein, the terms "energy bin" and "bin" refer to a particular range of measured photon energies between a minimum energy threshold and a maximum energy threshold. For example, a first bin may refer to counts of photons determined to have an energy greater than a threshold energy (referred to as a trigger threshold) and less than 20 keV, while a second bin may refer to counts of photons determined to have an energy greater than 20 keV and less than 40 keV, and so forth.

X-rays 107 from an X-ray tube 110 may be attenuated by a target 107 before interacting with the radiation detector material within the pixelated detector array 120. An X-ray photon interacting (e.g., via the photoelectric effect) with a pixelated radiation detector material generates an electron cloud within the material that is swept by an electric field to an anode electrode. The charge gathered on the anode creates a signal that is integrated by a charge sensitive amplifier (CSA) 131. There may be a CSA 131 for each pixel detector within the pixelated X-ray detector 120. The voltage of the CSA output signal may be proportional to the energy of the X-ray photon. The output signal of the CSA may be processed by an analog filter or shaper 132.

The filtered output may be connected to the inputs of a number of analog comparators 134, with each comparator connected to a digital-to-analog converter (DAC) 133 that inputs to the comparator a DAC output voltage that corresponds to the threshold level defining the limits of an energy bin. The detector circuitry 130 may be configured so that after the CSA voltage has stabilized (after the dead time), that voltage may be between two voltage thresholds set by two DACs 133, which determines the output of the comparators 134. Outputs from the comparators 134 may be processed through decision gates 137, with a positive output from a comparator 134 corresponding to a particular energy bin (defined by the DAC output voltages) resulting in a count added to an associated counter 134 for the particular energy bin.

Periodically, the counts in each energy bin counter 135 are output in signals 138 to the control unit 170.

The detector array of an X-ray imaging system may include an array of radiation detector elements, referred to herein as pixel detectors. The signals from the pixel detectors may be processed by a pixel detector circuit, which may sort detected photons into energy bins based on the energy of each photon or the voltage generated by the received photon. When an X-ray photon is detected, its energy is determined and the X-ray photon count for its associated energy bin is incremented. For example, if the detected energy of an X-ray photon is 24 kilo-electron-volts (keV), the X-ray photon count for the energy bin of 20-40 keV may be incremented. The number of energy bins may range from one to several, such as two to six. In an illustrative example, an X-ray photon counting detector may have four energy bins: a first bin for detecting photons having an energy between 20 keV and 40 keV, a second bin for detecting photons having an energy between 40 keV and 60 keV, a third bin for detecting photons having an energy between 60 keV and 80 keV, and a fourth bin for detecting photons having an energy above 80 keV. The greater the total number of energy bins, the better the material discrimination.

In X-ray imaging systems, a scanned object is exposed to an X-ray beam and attenuated photons from the X-ray beam are detected and counted by individual radiation detector pixels in a detector array. When an object (e.g., the object 10) is loaded in an X-ray imaging system, the X-ray beam may be heavily attenuated, and the number of photons detected by the detector array may be orders of magnitude less than the number of photons emitted from an X-ray source. For image reconstruction purposes, the radiation detector can be exposed to a direct X-ray beam without an intervening object located inside the X-ray imaging system. In such cases, the X-ray photon count rates in the X-ray imaging system may reach values of 100 million counts per second per square millimeter (Mcps/mm$^2$) or more. The detector array may be capable of detecting such a wide range of photon count rates.

Figure 2:
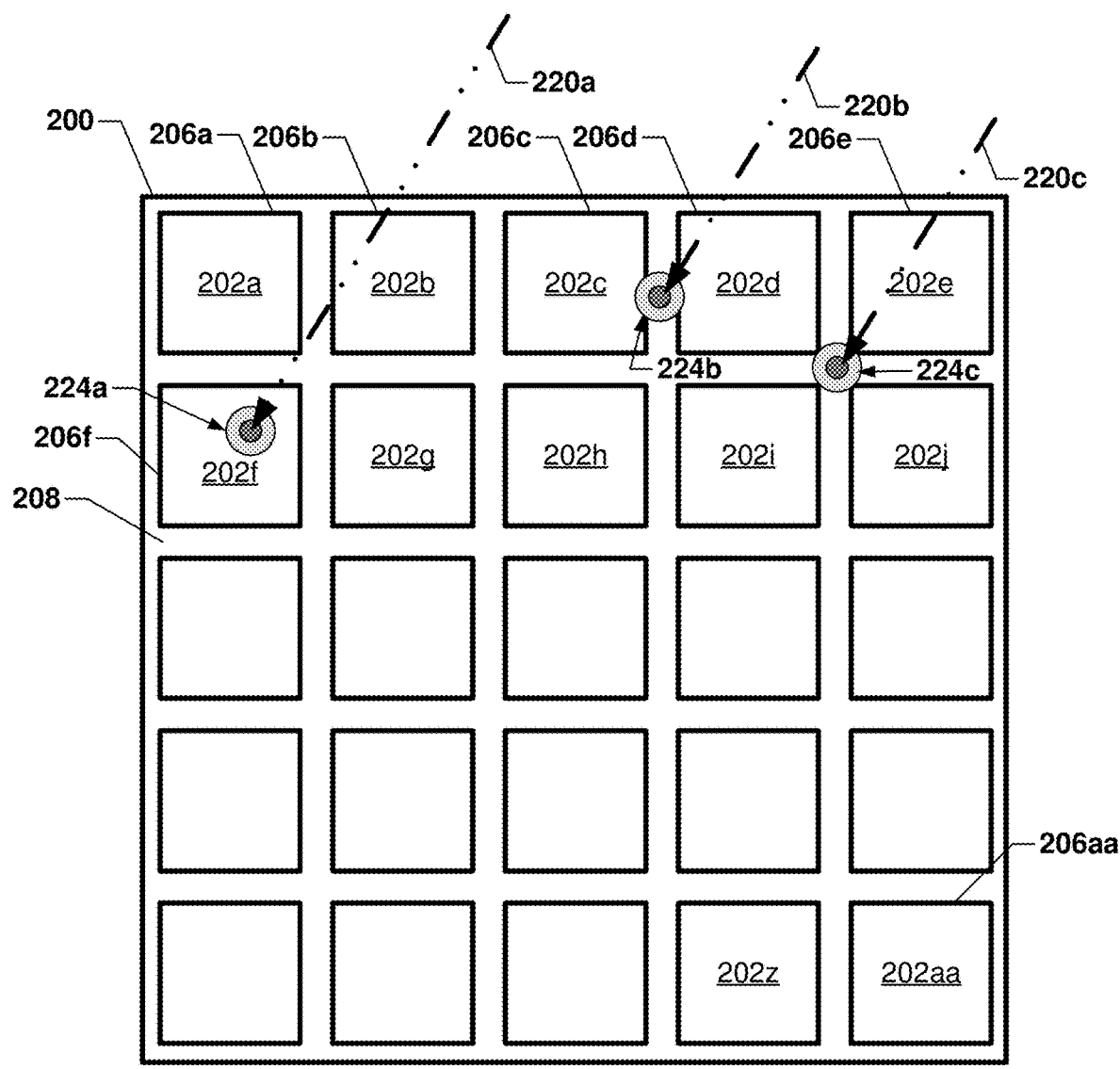
FIG. 2 is a conceptual top view diagram of a semiconductor pixel radiation detector illustrating X-ray interactions.

FIG. 2 is a top view of a portion of a pixelated radiation detector array 200 showing the plurality of pixels 202a-202aa formed by the anodes 206a206aa positioned on the CZT semiconductor crystal 208.

When an X-ray 220a interacts with atoms of the CZT semiconductor crystal 208 within the boundaries of a pixel detector defined by an anode 202f, the electrons within the cloud of ejected electrons 224a are gathered on the anode 206f and recorded as a count. The number of electrons (i.e., charge) collected on the anode 206f is reflective of the energy of the incoming photon, and thus a measurement of the energy of the detected photon can be determined from the charge or current detected on the anodes.

However, as illustrated with the example of incoming photon 220b, when a photon interacts with the CZT semiconductor crystal 208 near the edge of an anode or between two anodes 202c, 202d, the electrons within the generated electron cloud 224b may be shared between the anodes of the two adjacent pixels 202c, 202d. As a result of such sharing of the charge cloud, the net charge collected by each pixel detector anode 202c, 202d will be a fraction of the total number of electrons ejected by the photon absorption event. Thus, a single photon interaction in this example results in two counts in two adjacent pixel detectors, with each pixel detector recording a count in an energy bin that is lower than would be the case if there was no charge sharing (as in the example of photon 220a).

The electron cloud charge may be shared by more than two pixel detectors, such as illustrated with the example photon 220c. In this example, the photon interacts near or at the corner of four anodes 202d, 202e, 202i, 202j, resulting in sharing of the electron cloud 224c among the four adjacent anodes. Thus, a single photon interaction in this example results in four counts in four adjacent pixel detectors, with each recording a count in an energy bin lower than would be the case if there was no charge sharing (as in the example of photon 220a).

As the examples in FIG. 2 illustrate, charge sharing between pixel detectors results in more counts than actual photon interactions, but with energies (or in energy bins) lower than that of the incident photons. Further, charge sharing may result in uncertainty in the location of the photon interaction.

Figure 3A:
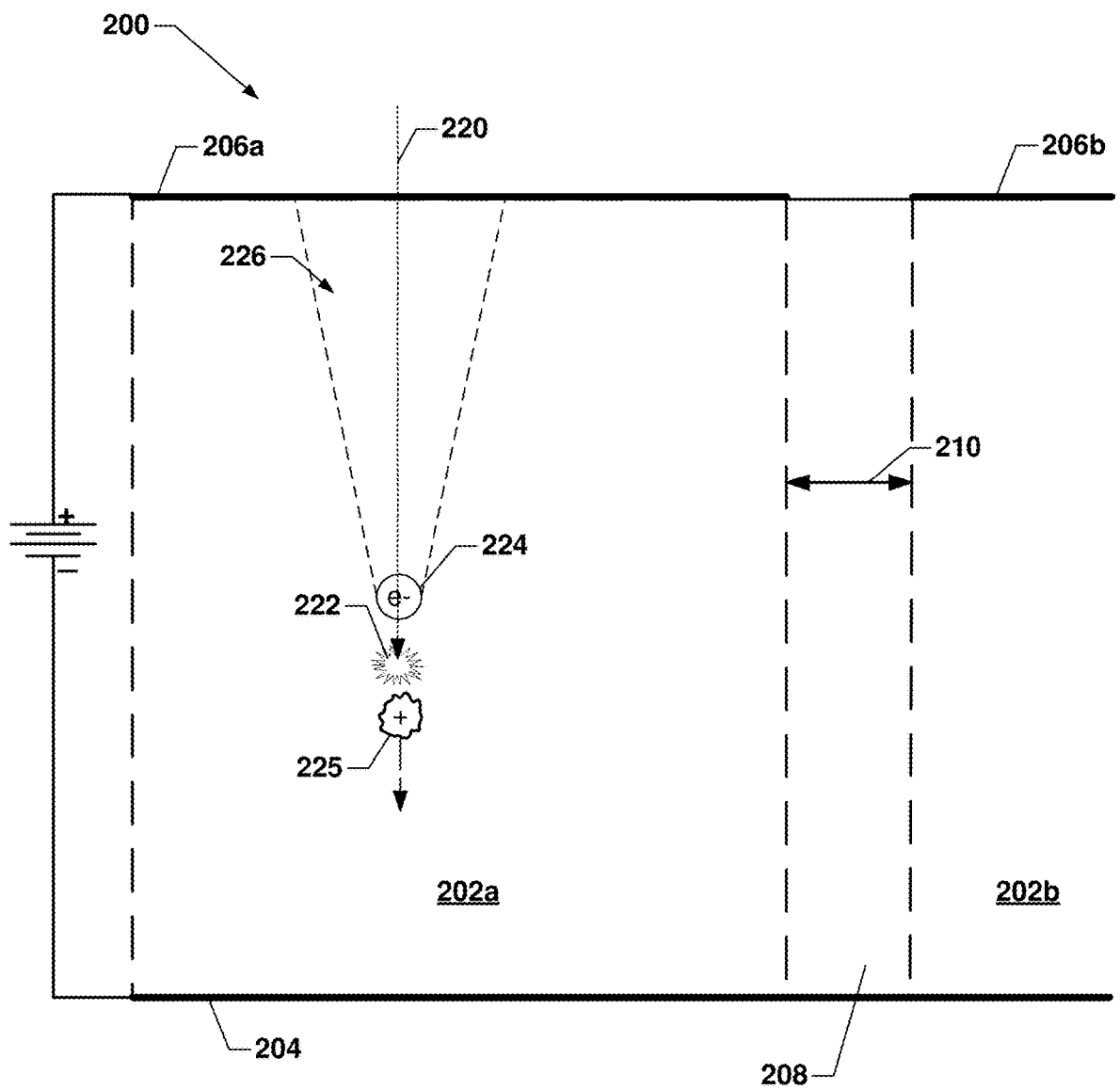
FIG. 3A is a conceptual cross section view diagram of a semiconductor pixel radiation detector illustrating an X-ray absorption and mechanisms for detecting and measuring the energy of the detected X-ray.
Figure 3B:
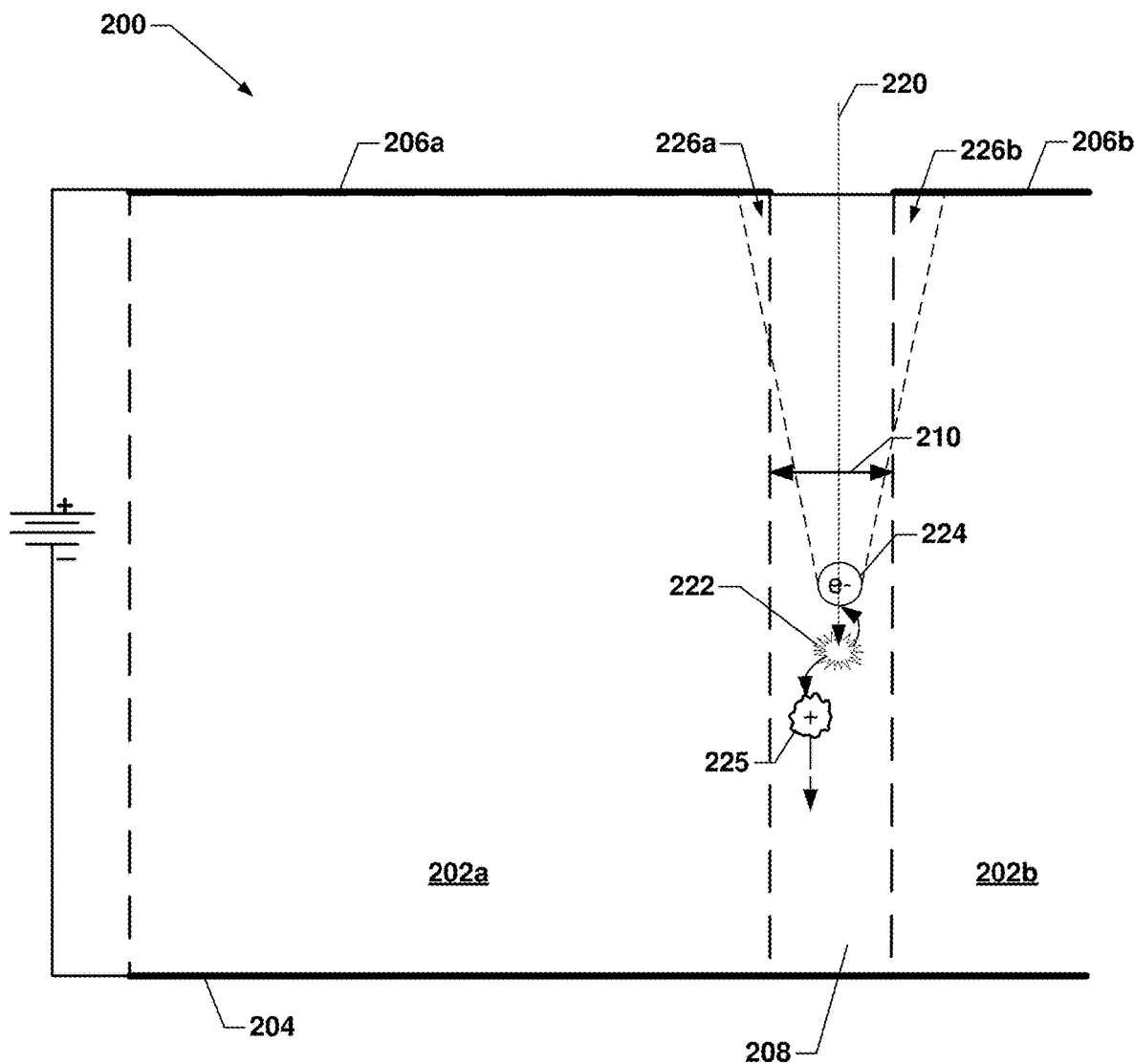
FIG. 3B is a conceptual cross section view diagram of a semiconductor pixel radiation detector illustrating an X-ray absorption occurring between adjacent detector pixels and the effect of measuring the energy of the detected X-ray between adjacent pixels.

FIGS. 3A and 3B provide cross-sectional representations of pixel detectors further illustrating the charge sharing phenomenon.

As an X-ray photon enters the CZT sensor volume of a detector and interacts with the atoms constituting that sensor it will deposit some, or all, of its energy. FIG. 3A illustrates a cross-sectional view of two pixels 202a, 202b within a CZT radiation detector array 200. Such a detector 200 may include a sheet of CZT semiconductor crystal 208 on which are applied to a cathode 204 and the anodes 206a, 206b that define each pixel 202a, 202b. The anodes 206a, 206b may be spaced apart by an inter-pixel gap 210. In typical radiation detector arrays 200, the thickness of the CZT semiconductor crystal 208 may range from 1 mm to 20 mm, the anodes 206a, 206b may have a side dimension of 0.1 mm to 3 mm, and the inter-pixel gap 210 may range from 0.01 mm to 0.5 mm.

When an X-ray 220 is absorbed via a photoelectric effect event 222 by an electron of an atom within the CZT semiconductor crystal 208, the energy of the X-ray photon is transferred to an ejected electron (not shown) that quickly slows down by ionizing nearby atoms thus generating a cloud of electrons 224 ejected into the conduction band of the semiconductor along the path of travel. The range of a photoelectron in CZT depends on the energy carried off by that electron. Each ejected electron creates a corresponding hole 225 of positive charge. The clouds of electrons (and holes) generated by photoelectrons are not uniform in charge density, because electron-hole production increases towards the end of the track of the photoelectron. A voltage is applied between the cathode 224 and anodes 206a, 206b causes the electrons 224 to drift to the anode 206a where they are collected as a signal as described above. Holes 225 similarly migrate towards the cathode 204. Diffusion and charge repulsion forces cause the electron cloud to expand (as shown at 226) by the time the electrons reached the anode 206a.

The term "cloud" is used to highlight the fact that the physical size of the electron charge is not a point but approximately a sphere with a certain radius. Each X-ray photon absorbed in the CZT detector generates several thousands of electrons, so even the initial charge has finite physical dimensions. The number of generated electrons can be estimated by dividing the incoming photon energy by the CZT ionization energy of 4.64 eV. For example, an X ray photon with an energy of 140 keV will produce about 30,000 electrons in the conduction zone, collectively carrying a charge of approximately 4.8 femto coulombs (fC).

As the detector needs to accommodate the time required for the charge cloud 226 to migrate to the anode 206a, a detector may be configured with a timer that controls when the charge on the anode should be registered as a signal indicative of the energy of the detected photon. In a typical detector, a threshold circuit coupled to each anode 206 may start such a timer when the charge on the anode exceeds a certain minimum threshold. The timer may then run for a brief period of time, referred to as a "dead time" time, during which charge is allowed to collect on the anode before the amount of charge is read by a CSA 131. In a high flux application, such as any of a number of X-ray imaging systems (e.g., an X-ray scanner), there is a significant probability that a second photon may be absorbed in the detector pixel during the dead time resulting in what is referred to herein as a pile up detection event. Unlike charge sharing, pile up events result in two photons counted as one photon detection with a total energy that is greater than either of the photons.

Because the energy of an incident photon 220 is reflected in the number of electrons in the cloud that are collected by the anodes 206a, 206b, the location of detection events and the measured energy of such events depends upon the location in the detector where energy is deposited from various photon-matter interactions. For example, as illustrated in FIG. 3B, an X ray photon 220 entering the detector 200 near the boundary of a detector pixel or within an inter-pixel gap 210 and undergoing a photoelectric absorption interaction 222 will result in a cloud of electrons 224 (and holes 225) that will be motivated by the electric field generated by the neighboring anodes 206a, 206b. As the electron cloud 224 drifts towards the anodes 206a, 206b, expanding due to mutual repulsion, a portion 226a of the electrons will be collected by one anode 206a and a portion 226b of the electrons will be collected by the neighboring anode 206b. Also, some electrons in the cloud 224 may interact with surface effects within the gap 210 between anodes 206a, 206b, and not be collected by either anode. Thus, an X ray photon 220 entering the detector 200 near the boundary of a detector pixel or within the inter-pixel gap 210 will result in signals in two detector pixels 202a, 202b, with each measured signal being a fraction of the total charge (i.e., electron cloud 224) created by the photoelectric effect interaction 222. Such an event is referred to herein as a charge sharing detection event.

Figure 4A:
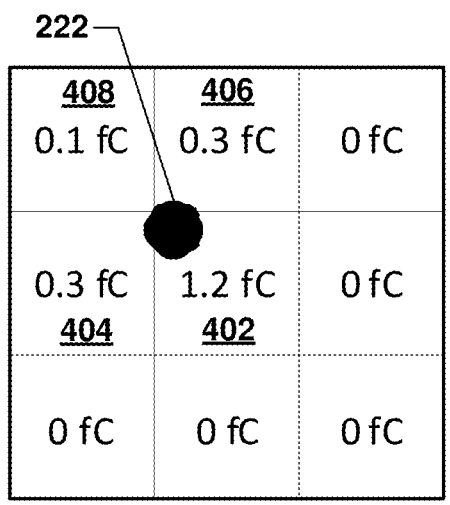
FIGS. 4A and 4B illustrate one mechanism for accounting for charge sharing among four pixel detectors by allocating the detected charges to one pixel detector with the greatest measured charge.
Figure 4B:
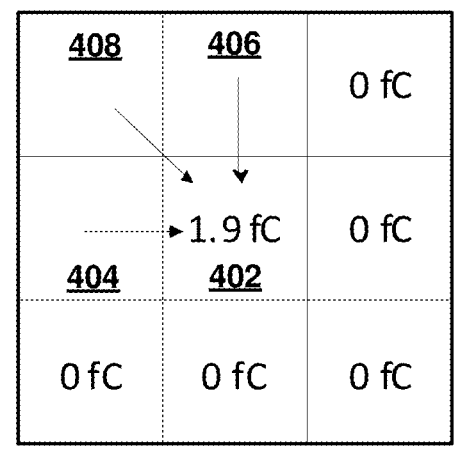

Various methods for resolving the locational ambiguity caused by charge sharing may be used. On method is illustrated in FIGS. 4A and 4B. Referring to FIG. 4A, an X-ray photon interacting with the detector near a corner of a pixel detector 402 may result in the electron cloud 222 being shared among the three adjacent pixel detectors 404, 406, 408. In this example of charge sharing, the pixel detector 402 in which the X-ray photon was absorbed recorded an accumulated charge of 1.2 femto-Coulombs (fC), side adjacent pixel detectors 404 and 406 recorded accumulated charges of 0.3 fC, while the corner-adjacent pixel detector 408 recorded an accumulated charge of 0.1 fC. This results in four counts but at lower energies than that of the incident X-ray photon. This effect of recording more counts but at lower energies causes a low energy tail in the detected X-ray spectrum in pixelated detectors.

In one method, a processor coupled to the detector (e.g., the ASIC 130) may be configured to recognize when two to four adjacent pixel detectors record an accumulated charge nearly simultaneously, such as within the dead time of the ASIC, and then allocate the charge of each of those pixel detectors to the one pixel detector that recorded the highest accumulated charge. To retain the energy information of the incoming photons, the system must recognize that a single photon event has spread its charge into a cluster of pixels, determine where the photon has most likely landed (usually selected as the pixel with the largest charge deposition), and assign all surrounding charge to that single pixel. This is illustrated in FIG. 4B in which the charges accumulated in each of the recording pixel detectors 402, 404, 406 and 408 are added and allocated to pixel detector 402 because its 1.2 fC recorded charge was highest.

A typical approach to this problem is to sum the charge in the detector as implemented in ASIC read-out electronics chips (e.g., the Medipix-3 for example). In such electronic circuitry, the analog charge may be summed in a 2×2 cluster before being compared to the detection threshold. This method of correction can solve both true charge-sharing and the effects of fluorescence photons (discussed later). The advantage of this approach (compared to signal processing after quantization) is that it can handle much higher interaction rates and also that even charges below the detection threshold may be summed as long as one pixel is triggered. However, since this correction has to be implemented in the ASIC architecture, this method complicates the chip design and is less flexible (e.g., it is hard-wired). There is also a practical limit of how quickly the summation process can be done. In MEDIPIX-3 the charge-sharing correction leads to maximum count rate being ten times smaller than without the correction. Typically, such a penalty is not acceptable in NDT applications. Therefore, other solutions need to be proposed and used, one of which is covered in this patent.

Various embodiments provide methods to counter charge-sharing effects by measuring the affect and reversing the changes it is creating in an iterative reconstruction process.

Charge-sharing may be characterized by one main parameter: percentage of charge-shared (PCS) events between the pixels defined as:

PCS=Number of Charge-Shared Events/Total_Events (%).

For pixelated detectors with a pixel pitch of 330 um, PCS is typically about 30-40%. However, the exact PCS value depends on the high-voltage (HV) being used in the detector, the detector thickness, material properties and state of the passivation in the interpixel gap, and other factors. Therefore, the PCS parameter cannot be predicted a priori. Detectors with smaller pixels have higher PCS and at some very small pitch values below 100 um PCS reaches 100%, meaning that all photon events result in the charge cloud being split between multiple pixel detectors. Conversely, pixelated detectors with larger pixels experience smaller numbers of charge0-shared events. However, even at a 500 um pitch a substantial number of photon detection events result in charge sharing. Thus, charge-sharing reconstructions will be beneficial in all designs of pixelate detectors, although the relative importance of the charge sharing effect increases for detector pitches below the 500 um range.

To fully account for charge sharing, a model of how X-rays interact with an imaging system and various phenomena that effect the measured energy spectrum may be developed.

The following phenomena can affect the X-ray energy spectrum measured by a pixelated detector in an X-ray imaging system: incomplete photon absorption within the detector due to finite thickness of the CZT sensor; beam hardening effects due to low energy photons being absorbed by the filter or object under inspection; the finite energy resolution (ER) characteristics of the CZT sensor; charge-sharing between pixel detectors of some photon detection events; X-ray fluorescence; and multiple photon interactions within the response time of detector circuitry (referred to herein as "pile-up" effects). The effects of these phenomena may be taken into account when determining what the measured X-ray spectrum should look like depending on the energy and current applied to the X-ray tube, characteristics of the detector array (e.g., materials and pixel size), and the object placed between the X-ray tube and the detector.

Figure 5A:
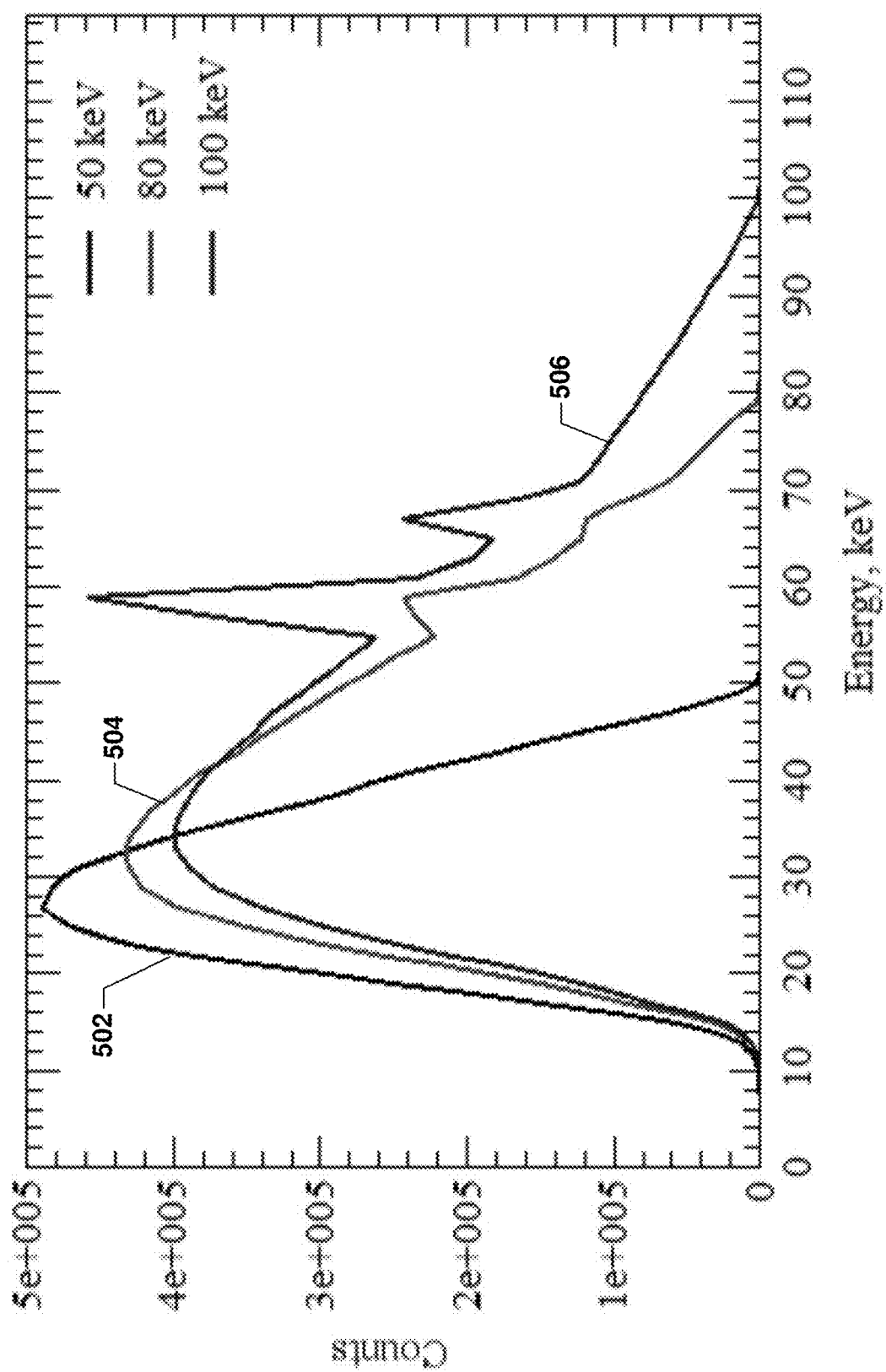
FIG. 5A is a graph showing X-ray spectra emitted by an X-ray tube operating at 50 keV, 80 keV and 100 keV.

The shape of the transmitted X-ray spectra from an X-ray tube as a function of the energy and current applied to the X-ray tube is well known. Numerous on-line tools, such as https://www.oem-products.siemens-healthineers.com/X-ray-spectra-simulation, can be used to determine the spectrum of X-rays emitted from an X-ray tube at a given tube voltage. For example, FIG. 5A illustrates the transmitted X-ray spectra for different X-ray tube voltages typically used in NDT applications. Characteristic X-ray count peaks are visible at X-ray tube voltages of 80 keV and 100 keV, but not at X-ray tube voltages of 50 keV due to a tungsten target being used in the X-ray tube. This is because the tungsten characteristic peaks are at 59 keV and 67 keV.

One factor that has a significant impact on the recorded X-ray spectrum is the finite absorption characteristics of the detector. If a CZT detector was thick enough, the detector material would absorb and thus detect all incoming X-ray photons. However, in practice the CZT thickness is limited to a thickness that is acceptable to avoid polarization effects. Typical thickness for high-flux CZT detector is 2 mm, but somewhat thinner (1.6 mm) and thicker (2.2 mm) sensors are being used as well. For example, for X-ray photons of 100 keV the stopping probability is only 50% at 1 mm thickness of CZT but increases to 76% at 2 mm and reaches 88% at 3 mm.

Figure 5B:
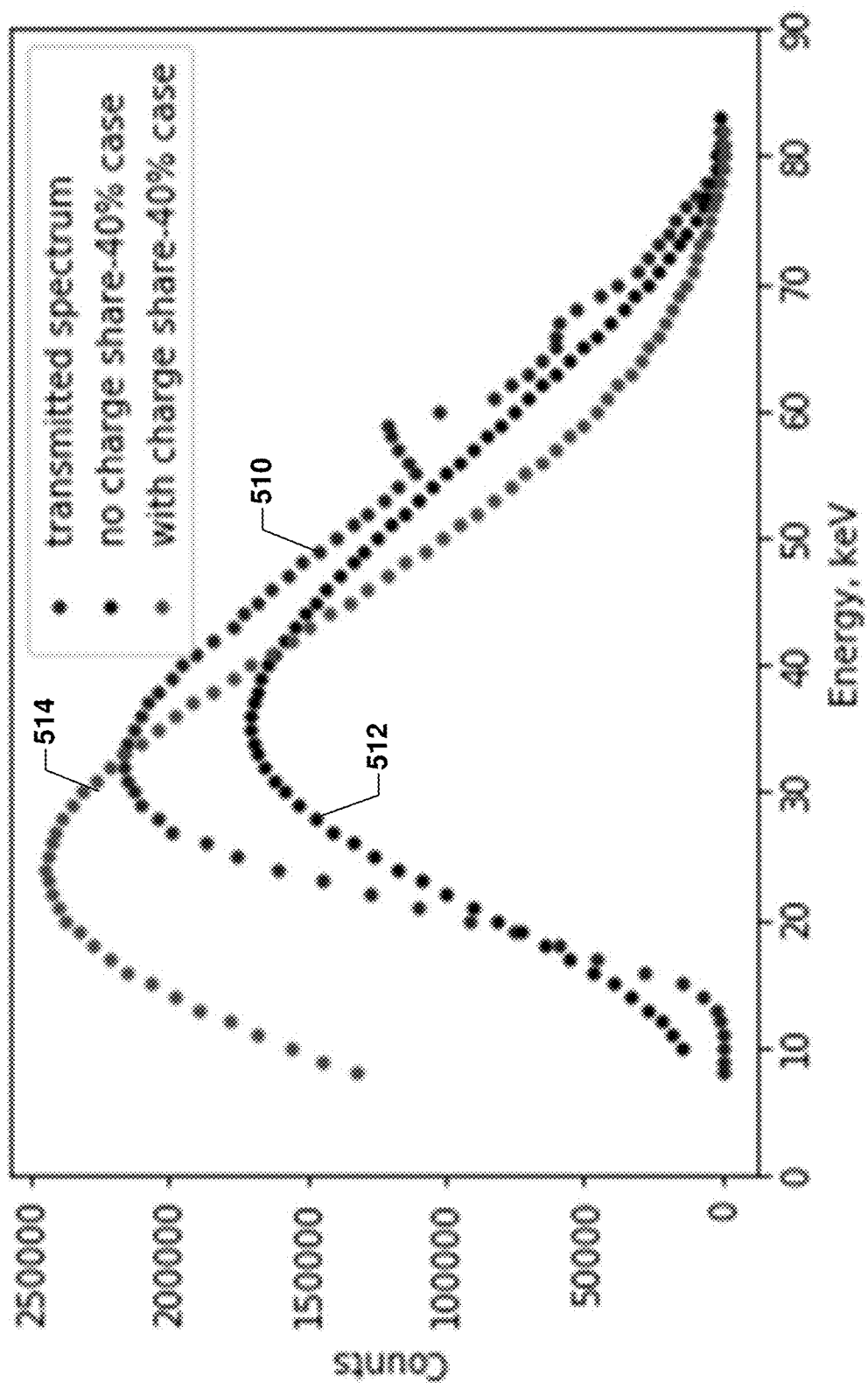
FIG. 5B is a graph of simulation results comparing a transmitted X-ray spectrum to the spectrum that would be measured by a pixelated detector with no charge sharing and with 40 percent charge sharing among pixel detectors.

Incomplete absorption leads to suppressed counts of photons of high energy in the measured spectra because higher energy photons are more likely to pass through the finite thickness of CZT detector without detection. This is illustrated in FIG. 5B, which shows how a transmitted X-ray spectrum (dotted line 510) may be measured by a CZT detector (dotted line 512) due to incomplete absorption.

Another factor that has a significant impact on the recorded X-ray spectrum is charge sharing between pixel detectors. FIG. 5B shows simulations of the X-ray spectra (dashed line 510) transmitted by an X-ray tube with a voltage of 80 keV, the detected X-ray spectrum with no charge-sharing (dashed line 512), and the detected X-ray spectrum with charge-sharing (dashed line 514) that assumes that 40% of all photons are charge-shared among pixel detectors. As this simulation shows, charge sharing results in fewer counts at higher energies and more counts at lower energies than in the incident X-ray spectrum, as charge sharing results in fractions of the electron cloud from one photon absorption being detected in two or more pixel detectors as described above.

Figure 5C:
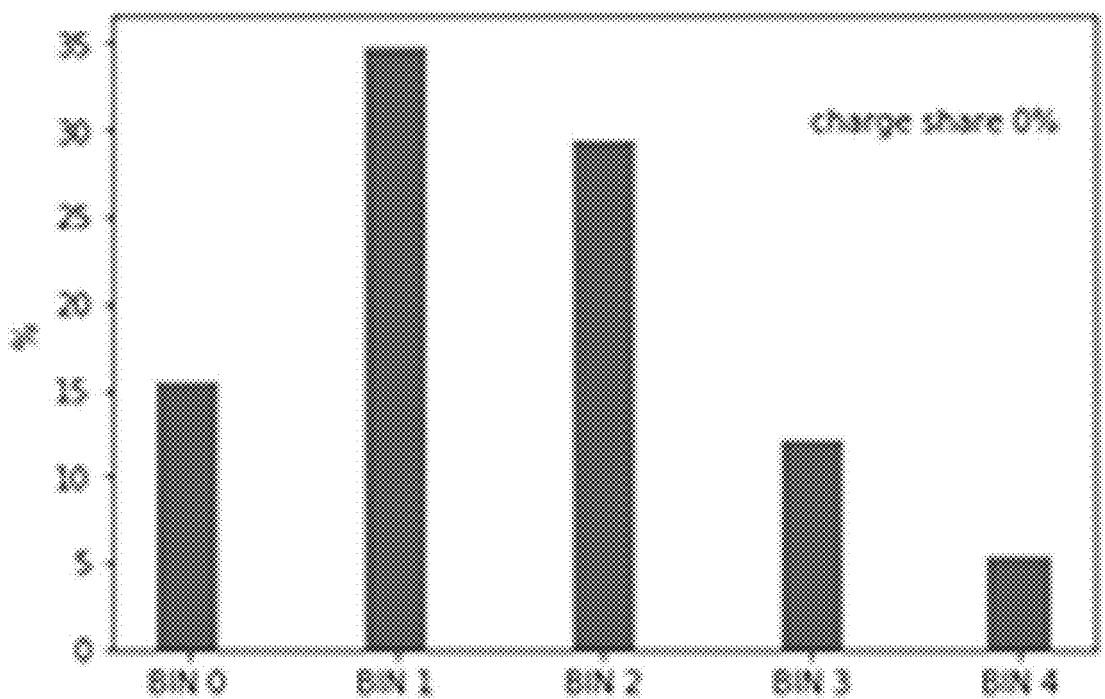
FIGS. 5C-5H are graphs of simulation results showing the energy spectrum of X-rays generated with an X-ray tube operation at 120 kVpp as measured by a pixelated detector in energy bins at 16, 30, 50, 70, 90 and 120 keV with a percentage of charge sharing of 0%, 20%, 40%, 60%, 80% and 100%, respectively.
Figure 5D:
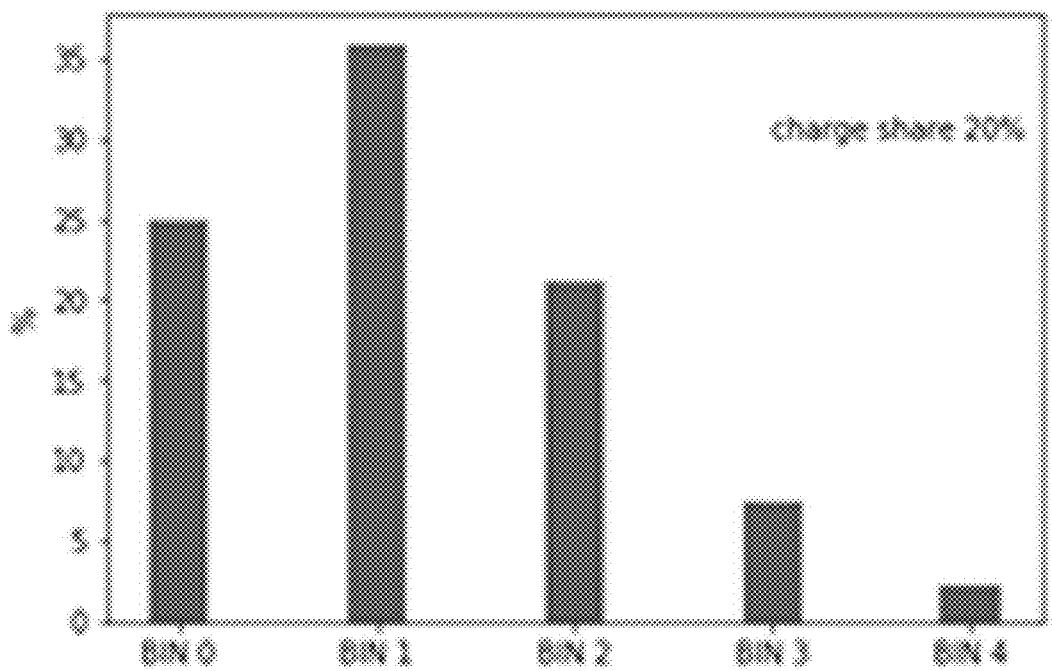
Figure 5E:
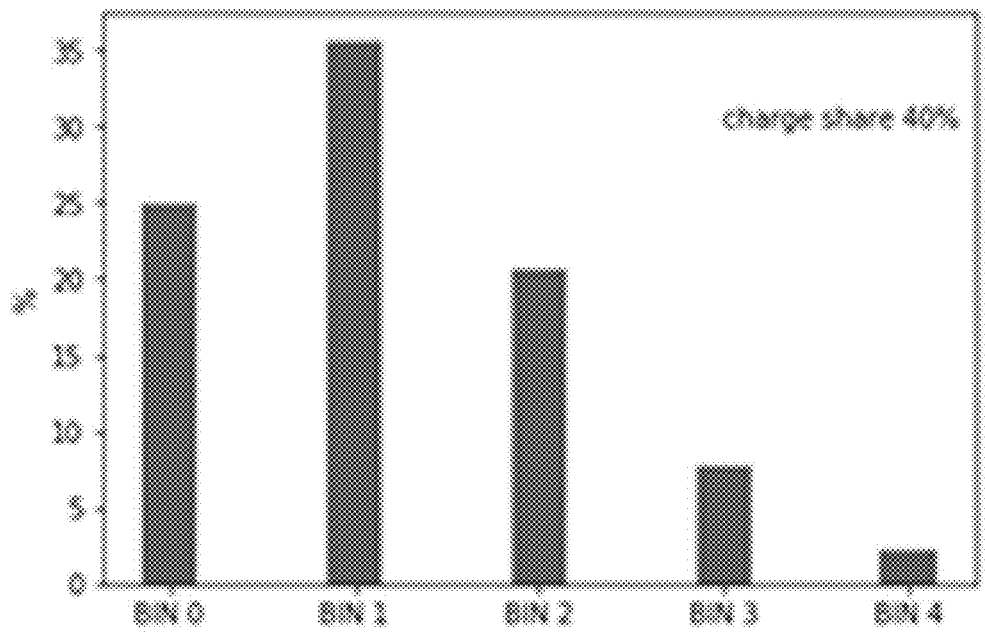
Figure 5F:
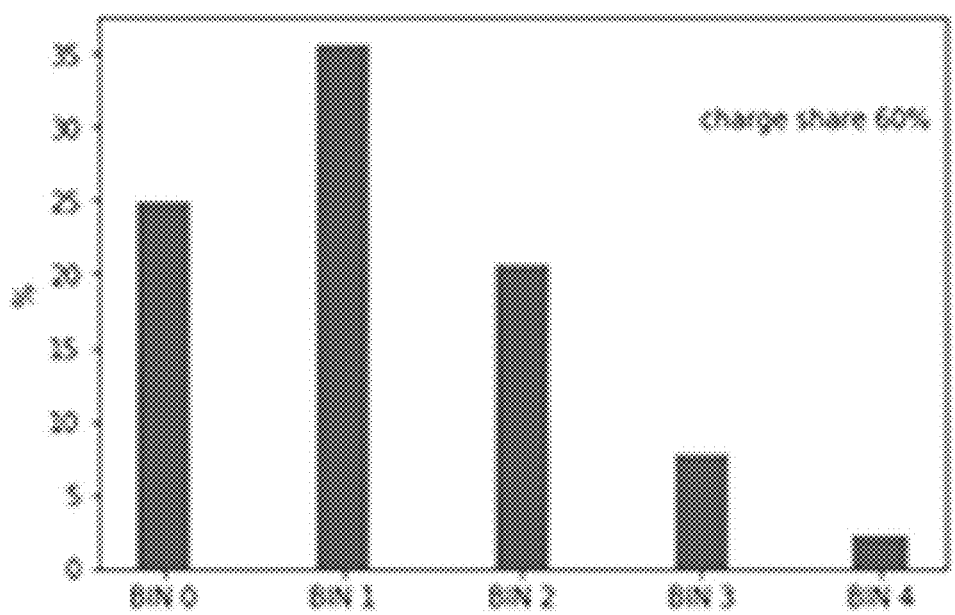
Figure 5G:
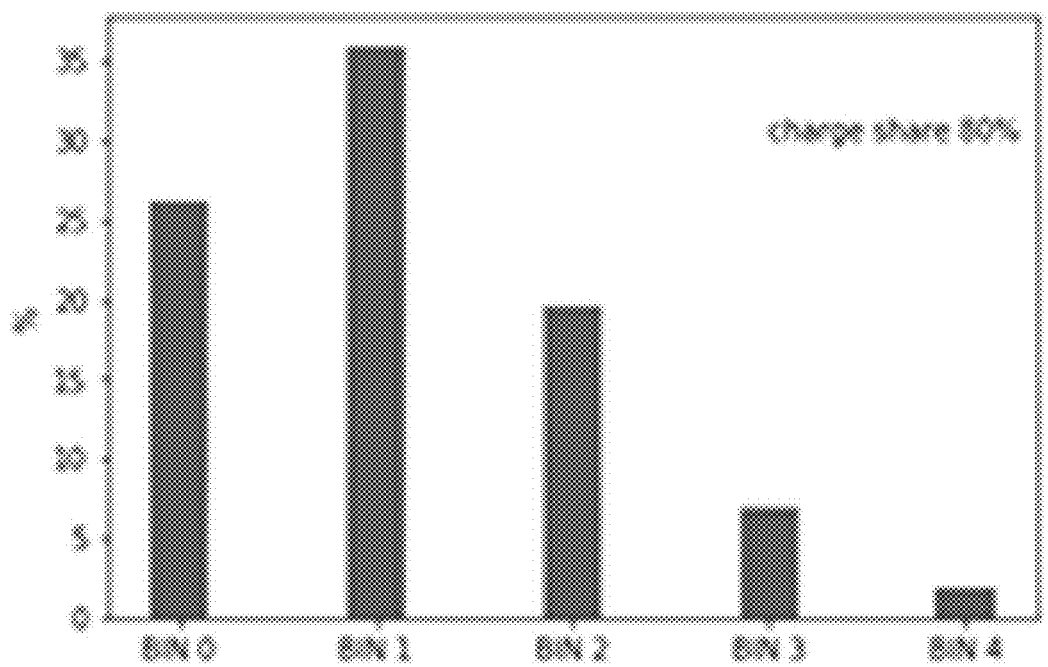
Figure 5H:
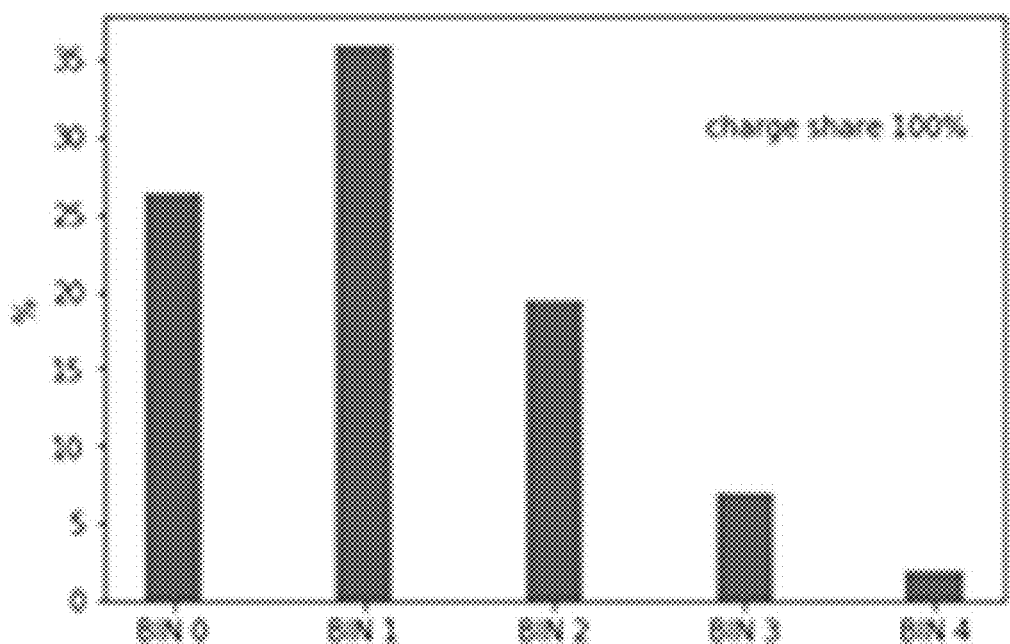
Figure 5I:
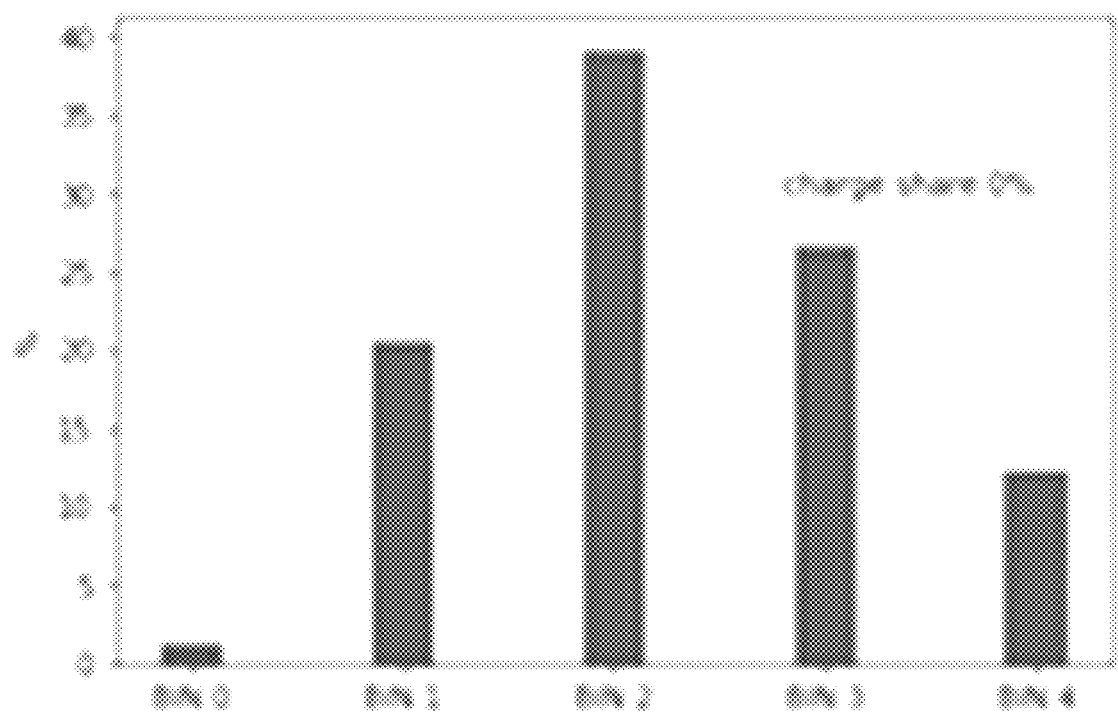
FIGS. 5I-5N are graphs of simulation results showing the energy spectrum of X-rays generated with an X-ray tube operation at 120 kVpp that have passed through a 1 mm thick copper filter as measured by a pixelated detector in energy bins at 16, 30, 50, 70, 90 and 120 keV with a percentage of charge sharing of 0%, 20%, 40%, 60%, 80% and 100%, respectively.
Figure 5J:
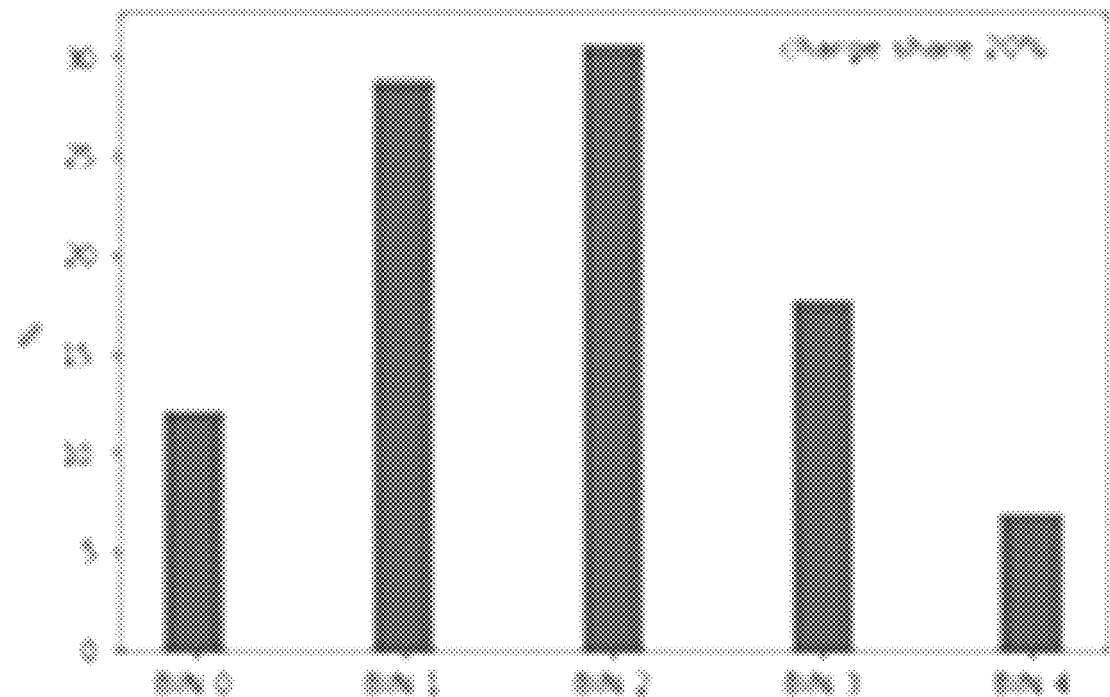
Figure 5K:
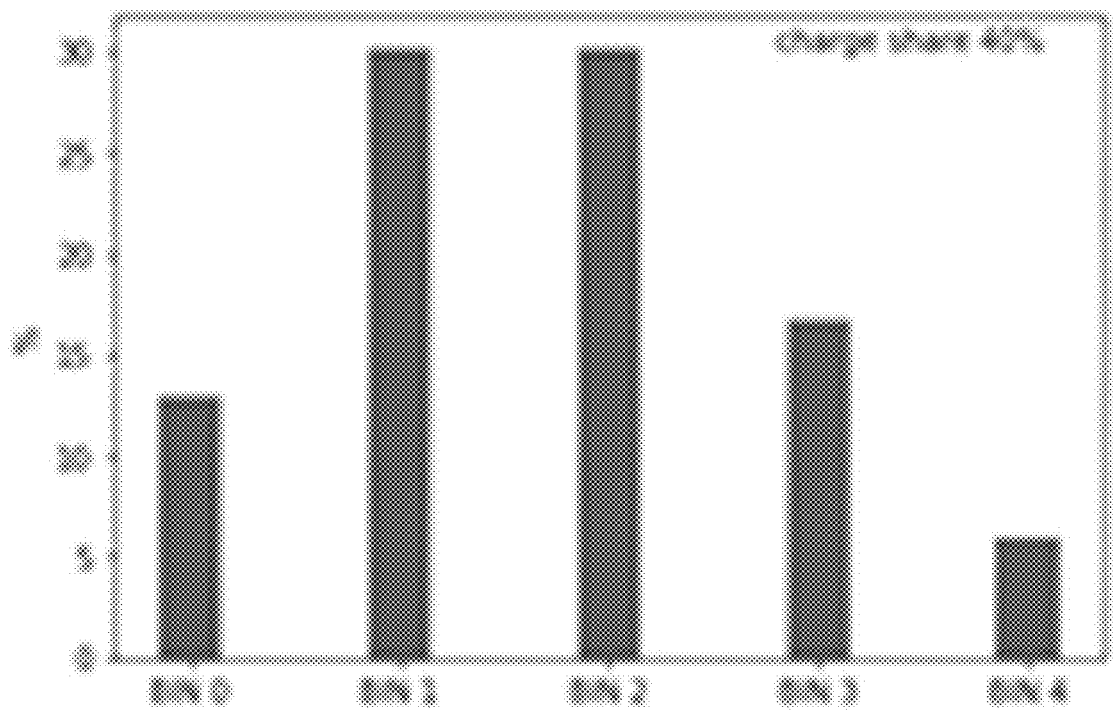
Figure 5L:
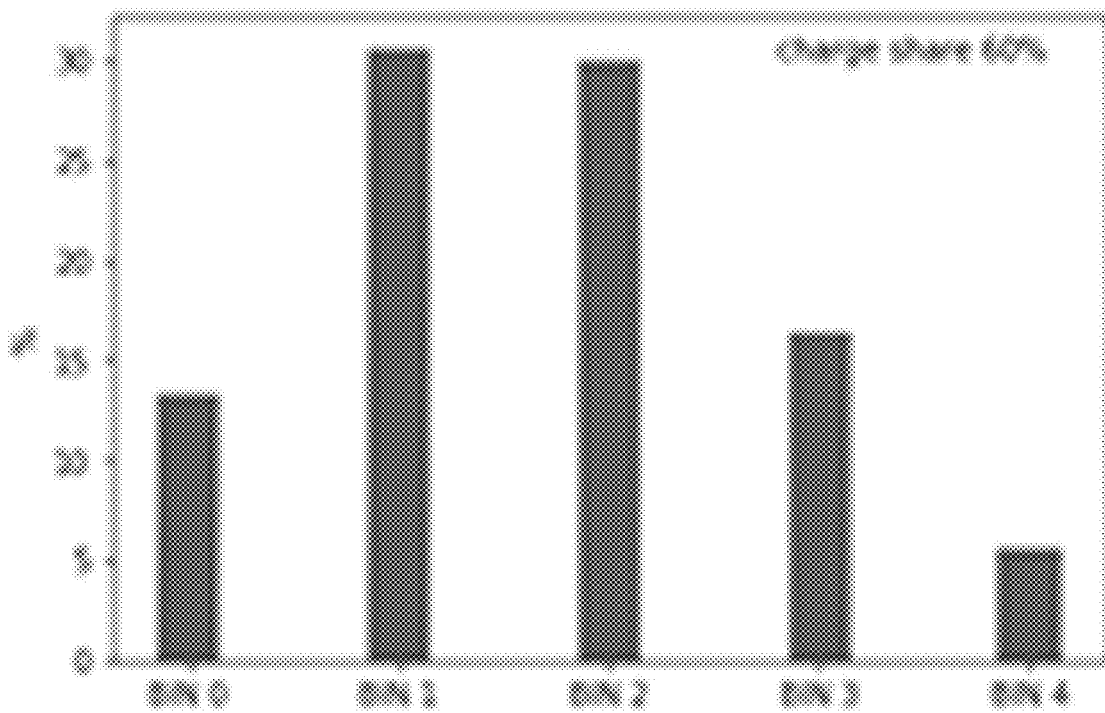
Figure 5M:
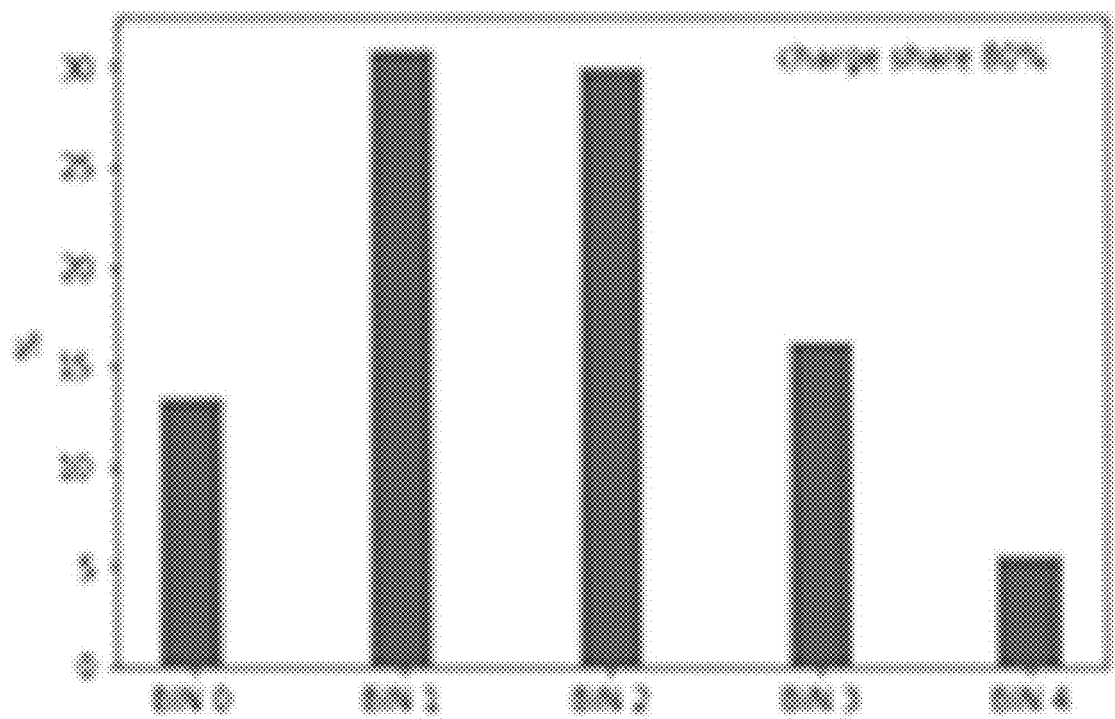
Figure 5N:
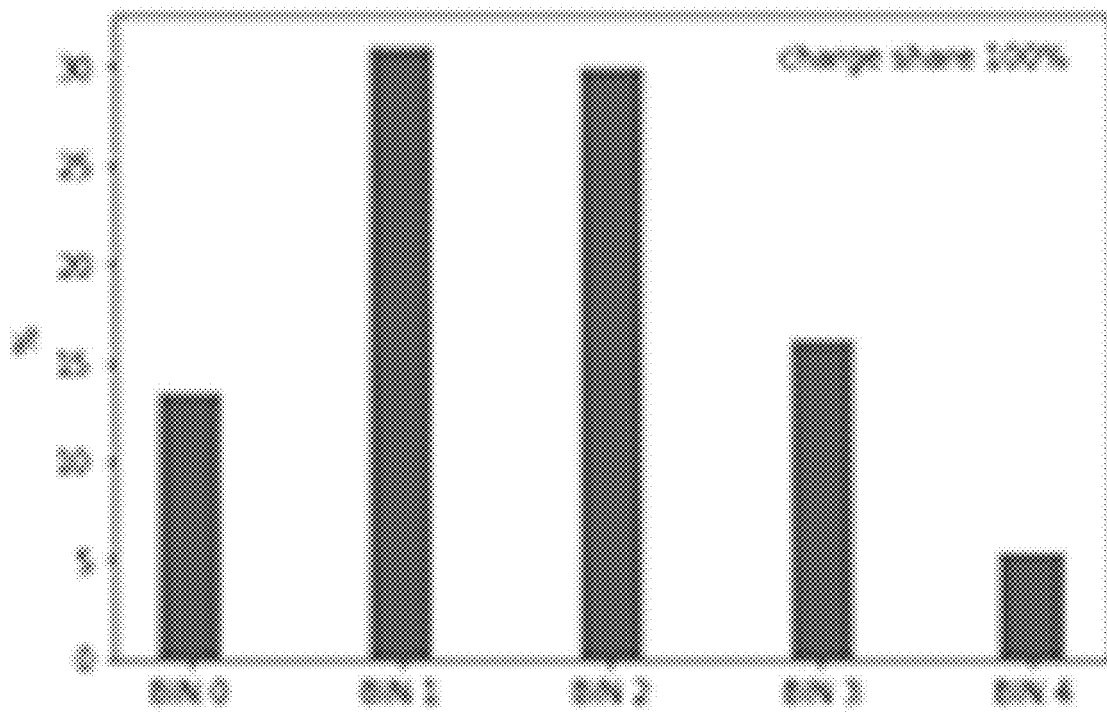

In a typical X-ray imaging system, the energy spectrum of the X-ray photons is measured by counting the number of photons detected in each of the number of energy bins. This is illustrated in FIG. 5C, which shows the energy spectrum of X-rays generated within X-ray tube operating at 120 kVpp as measured by a CZT pixelated detector in energy bins at 16, 30, 50, 70, 90 and 120 keV assuming no charge sharing. The effect of charge sharing on the X-ray energy spectrum measured with a finite number of energy bins can be seen by comparing the energy spectrum illustrated FIG. 5C with the energy spectra illustrated in FIGS. 5B-5H, which show the measured energy spectrum of X-rays with charge sharing percentages of 20%, 40%, 60%, 80% and 100%, respectively. As can be seen in these figures, charge sharing results in reduced counts in the higher energy bins and increased counts in the lower energy bins, as the energy of single photons a recorded and multiple pixel detectors based on the respective amount of shared charge.

Another factor that has a significant impact on the recorded X-ray spectrum is the energy resolution (ER) of the detector. The spectral X-ray detector sub-system measurements are limited by the energy resolution resulting from imperfect CZT sensor and the ASIC electronics. Typical values of the energy resolution span a range of 6 to 12 keV. The non-zero energy resolution causes broadening of the energy bins as photons having an energy within the energy resolution of a bin threshold (i.e., near the minimum or maximum energy bounds of the energy bin) may be recorded in the next lower or higher energy bin.

The interactions of X-ray photons with the CZT crystal involves a very complex chain of events. However, Monte Carlo simulations have shown that the primarily created electron sphere created in the primary interaction of an X-ray photon with a CZT atom is quite small for the photon energies relevant in X-ray photon counting. Subsequent processes like diffusion and repulsion within the electron cloud as it migrates toward the anode will spread the electron cloud. Consequently, the size of the electron cloud created by electron-scattering only may be neglected in some cases or accounted for with a small correction.

An effect that can impact the recorded X-ray spectrum is X-ray fluorescence. The impact of X-ray fluorescence on the measured X-ray spectra can be similar to charge sharing. In practice it is typically difficult to distinguish between X-ray fluorescence and charge sharing effects and they can effectively be lumped together and treated together through the same analysis as described herein.

When an X-ray photon interacts with the detector crystal, charges are generated in a cascade of events. A photoelectric absorption, as described herein, occurs for most of photon interactions with the CZT detector materials within the energies of interest in most NDT applications. In a photoelectric interaction with any of the tellurium, cadmium or zinc atoms in a CZT detector, the X-ray photon is absorbed by a K, L, M, or higher shell electron, which is ejected from the atom causing a shell vacancy. The ejected electron which will travel some distance before it interacts with another atom, displacing electrons as it slows down forming the clouds of electrons and holes in the semiconductor material. The resulting K-shell vacancy will be filled by an electron, which emits an X-ray that carries energy away from the initial interaction site but will undergo photoelectric absorption elsewhere in the crystal. When a photoelectric absorption of the initial X-ray photon creates a K-shell vacancy, the vacancy will be immediately filled by an electron that emits a fluorescence X-ray. The fluorescence X-ray carries energy away from the initial interaction site before that X-ray interacts with an electron of another atom, such as in a photoelectric absorption that creates another electron cloud some distance from the initial electron cloud. Thus, the fluorescence X-ray from a K-shell absorption causes some spreading of the cloud of electrons formed in the CZT detector. However, if the L, M, or higher shells have been ionized, the products of these low-energy interactions will have a range of less than 5 μm, and thus, practically, will not contribute to the spreading of the electron cloud.

The X-ray shell energy of zinc (Zn) is too low for a fluorescent X-ray of a Zn atom to travel more than few μm before being absorbed. For the case of Cadmium (Cd) and Tellurium (Te), a K-shell fluorescent X-ray emission will be absorbed within about 50 μm from the origin, which may somewhat inflate the primary electron cloud by such effects, although not uniformly since there is a large ratio of non-K-shell scattering events.

Due to the distance traveled by a fluorescent X-ray before absorption, some K-shell fluorescent X-ray emission events can end up being detected in neighboring pixel detectors. As a result, additional spikes in the spectral response may be measured between 23 keV and 32 keV that add up to true charge-shared events. However, if the data analysis is confined to X-ray energies above 32 keV, the effects of fluorescence X-rays can be neglected.

Another effect that can impact the recorded X-ray spectrum is Compton Scattering. At the X-ray energies of interest in NDT imaging, only about 2.5% of X-ray photons of 70 keV will be Compton Scattered (also referred to as incoherent scattering), although this percentage will increase to 12% for X-ray photons of 120 keV. When the original X-ray ray photon undergoes Compton or coherent scattering instead of a photoelectric absorption, some of the photon's energy is imparted to an electron at the site of scattering, and the scattered photon with reduced energy will undergo photoelectric absorption elsewhere in the crystal.

Another effect that can impact the recorded X-ray spectrum is due to more than one X-ray photon interacting with a detector pixel during the response time (also referred to as the dead time) of ASIC circuitry that measures and records photon detections. The ASIC circuitry that detects and records photon detections is configured to wait a short period of time following sensing of an increase in voltage on a detector anode to enable the full electron cloud to migrate to the anode, and thus provide a measure of the full energy of the photon. During this dead time delay, a second (or third) photon may interact with the same detector pixel in what is referred to as a "pile up" event. A pile up event results in the anode collecting charge from two (or more) electron clouds by the end of the dead time. In such events, a single detection event is counted with an energy greater than that of the first interacting photon. Thus, pile up effects distort the X-ray spectra by increasing counts at high energies. The probability of pile up events depends on the X-ray flux, the size of the pixel detector, and the dead time of the ASIC circuitry that measures and records photon detections.

Pile up effects can be minimized by measuring the X-ray spectra under low (mA) X-ray tube currents (i.e., low X-ray flux) conditions, thereby enabling X-ray spectra model validation without the influence of pile-up effects. Non-destructive testing is typically done under conditions that result in little to no pile up events. However, for other applications, such as X-ray scanning, a pile-up model may be needed. In such cases, pile-up modeling and an appropriate correction for such effects may be developed concurrently with charge-sharing corrections.

Another factor that has a significant impact on the recorded X-ray spectrum is charge sharing between pixel detectors. FIG. 5B shows simulations of the X-ray spectra (dashed line 510) transmitted by an X-ray tube with a voltage of 80 keV, the detected X-ray spectrum with no charge-sharing (dashed line 512), and the detected X-ray spectrum with charge-sharing (dashed line 514) that assumes that 40% of all photons are charge-shared among pixel detectors. As this simulation shows, charge sharing results in fewer counts at higher energies and more counts at lower energies than in the incident X-ray spectrum, as charge sharing results in fractions of the electron cloud from one photon absorption being detected in two or more pixel detectors as described above.

In a typical X-ray imaging system, the energy spectrum of the X-ray photons is measured by counting the number of photons detected in each of the number of energy bins. This is illustrated in FIG. 5C, which shows the energy spectrum of X-rays generated within X-ray tube operating at 120 kVpp as measured by a CZT pixelated detector in energy bins at 16, 30, 50, 70, 90 and 120 keV assuming no charge sharing. The effect of charge sharing on the X-ray energy spectrum measured with a finite number of energy bins can be seen by comparing the energy spectrum illustrated FIG. 5C with the energy spectra illustrated in FIGS. 5B-5H, which show the measured energy spectrum of X-rays with charge sharing percentages of 20%, 40%, 60%, 80% and 100%, respectively. As can be seen in these figures, charge sharing results in reduced counts in the higher energy bins and increased counts in the lower energy bins, as the energy of single photons a recorded and multiple pixel detectors based on the respective amount of shared charge.

Another factor that has a significant impact on the recorded X-ray spectrum is beam hardening effects due to absorption by a filter or an object under examination. Using various filters to attenuate X-ray signal is common in X-ray scanning. Attenuation filters are used to regulate the dose to the subject of examination. Bow-tie filters are used to limit exposure at the edges of the field-of-view (FoV). K-edge filters are used to separate low and high energy photons. Signal attenuation and related beam hardening are also significant consequences of measuring the object in the scanner. In X-ray laboratory practice, simple filters of copper foil or similar medium like lead are used. Including a filter in the X-ray beam tends to harden the spectrum as lower energy photons are more likely to be blocked than higher energy photons. This is illustrated in FIGS. 5I-5N, which show the energy spectrum of X-rays generated with an X-ray tube operation at 120 kVpp that have passed through a 1 mm thick copper filter as measured by a CZT pixelated detector in energy bins at 16, 30, 50, 70, 90 and 120 keV with a percentage of charge sharing of 0%, 20%, 40%, 60%, 80% and 100%, respectively. These figures show how the counts in lower energy bins are suppressed compared to the counts in the higher energy bins, particularly when there is no charge sharing as in the example illustrated in FIG. 5I. Charge sharing tends to have the opposite effect of softening the energy spectrum by increasing the counts in lower energy bins, as can be observed in the effect on the energy bin counts of increasing charge sharing percentage shown in FIGS. 5J-5N.

Figure 7:
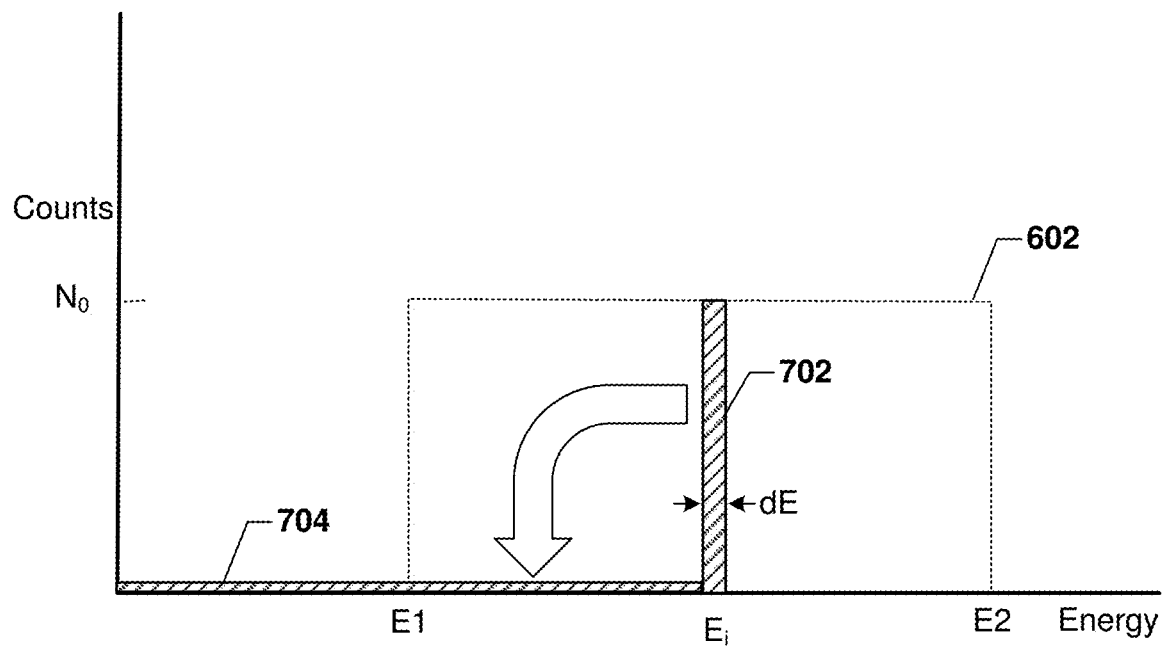
FIG. 7 is a graph illustrating how photon energies within a narrow band or slice of energy (dE) of a notional flat X-ray spectrum would be spread across lower energies due to effects of charge sharing.

The effects of charge sharing on an X-ray spectrum may be estimated by calculating how charge sharing decreases counts at higher energies and increases counts at lower energies. This shifting of the energy spectrum can be visualized by considering the ideal case of a rectangular X-ray spectrum in which the number of detections or counts per unit of X-ray energy (kEV) is constant between a first energy E1 and a second higher energy E2. As illustrated in FIG. 7. Assuming such a flat energy spectrum, the number of photons interacting with the detector within a unit time within a small increment dE 702 at energy $E_i$ of the energy spectrum 602 will be constant (NO) across the energy range between E1 and E2. Thus, the total number of photons counted without accounting for charge sharing effects with the be equal to the sum from $E_i$=E1 to $E_i$=E2 of N0*dE, which is $N_0$*(E2−E1).

Charge sharing has the effect of causing some of the energy of the detected photon to be recorded in two or more pixel detectors, with the amount of energy shared ranging from 100% to 0% based on several factors, including how close to the boundary of a pixel detector that the photon is absorbed. For analysis purposes, it can be assumed that the share of energy of photons detected with charge sharing in every small portion dE 702 at energy $E_i$ of the X-ray energy spectrum 604 is distributed uniformly. For example, under this assumption, 60 kEV photons detected with 100% charge sharing would exhibit a flat detected energy distribution from 59 kEV to 1 kEV, such that each 60 kEV photon would be recorded as split into 59+1, 58+2 . . . 30+30 . . . 2+58, 1+59 keV (assuming 1 keV intervals) etc. Each incremental slice contribution to the charge-shared spectra Y(Energy) can be expressed as $dE/E_i$.

Figure 8:
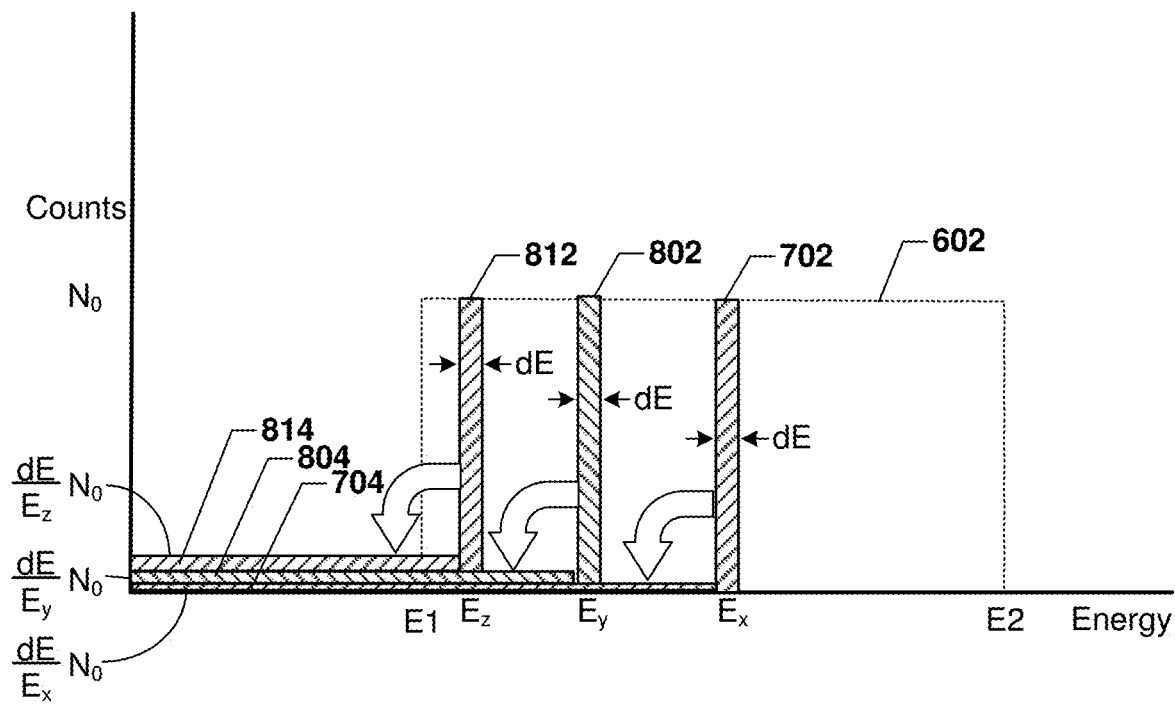
FIG. 8 is a graph illustrating how photon energies within multiple energy slices (dE) of a notional flat X-ray photon energy spectrum spread across lower energies add up to produce a measured X-ray photon energy spectrum that differs from the incident X-ray photon energy spectrum due to effects of charge sharing.

Thus, as illustrated in FIG. 8, each small portion dE at energies $E_x$ 702, $E_y$ 802, and $E_z$ 812 of the X-ray photon energy spectrum would result in a flat distribution of detected energies 704, 804, 814 from 0 kEV up to the energy of the slice dE. For example, the count of photons in energy slice dE at energy $E_x$, equal to $dE*N_0$, would be spread over energies from 0 to energy $E_x$ as illustrated in the flat distribution of counts 704 of value $dE/E_x*N_0$. Similarly, the count of photons in energy slice dE at energy $E_y$ would be spread over energies from 0 to energy $E_y$ as illustrated in the flat distribution of counts 804 of value $dE/E_y*N_0$. Further, the count of photons in energy slice dE at energy $E_z$ would be spread over energies from 0 to energy $E_z$ as illustrated in the flat distribution of counts 814 of value $dE/E_z*N_0$. With the number of photons of any energy E being equal to the constant No, the flat distribution of energies 704 for each energy increment dE would be equal to $2N_0*dE/E_i$.

Note that the lower the original photon energy E, the higher the contribution to the distribution of detected energies between 0 kEV up to the energy E of the slice dE, as the total number of counts within dE is spread over a smaller energy range. This is also illustrated in FIG. 8.

Figure 6:
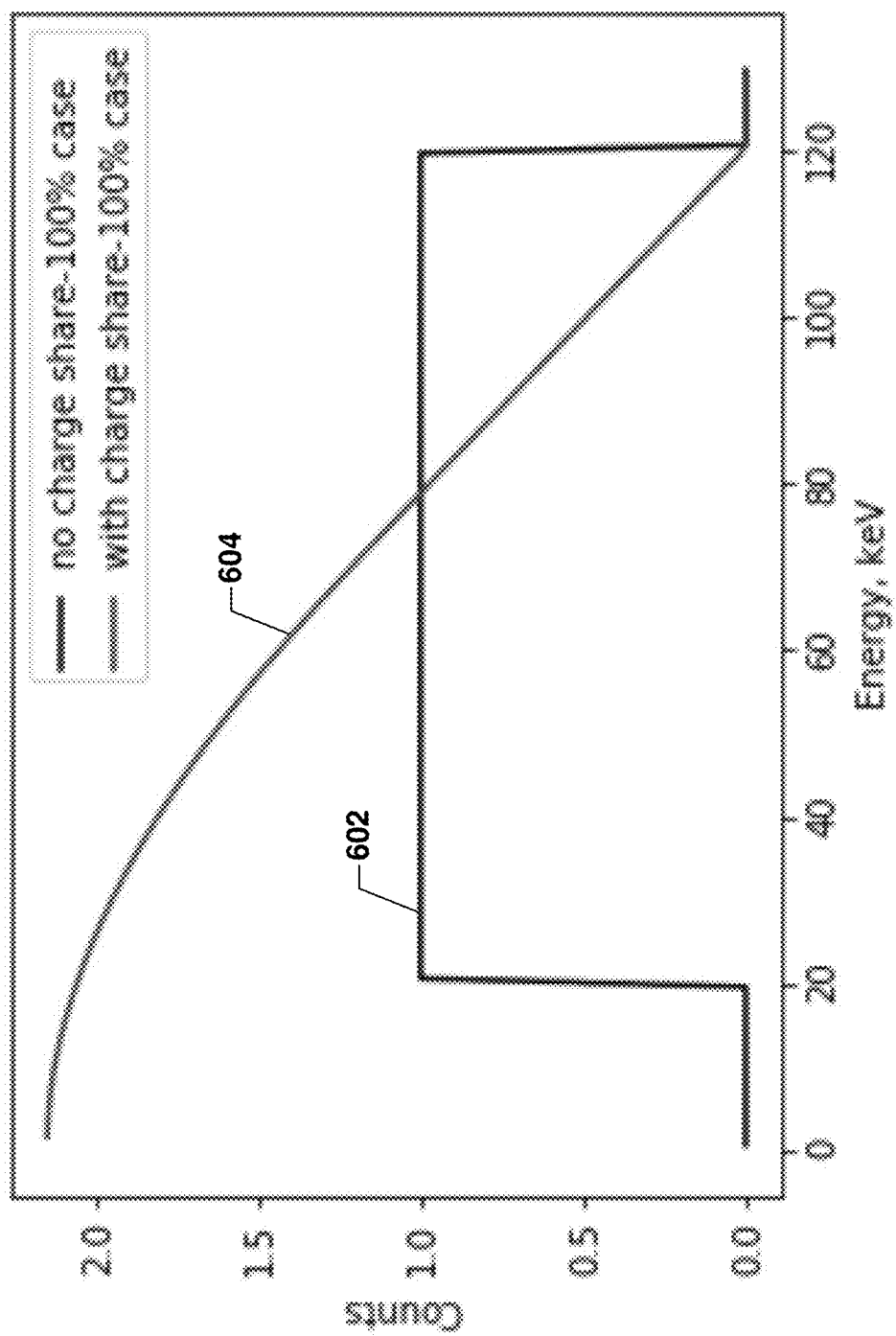
FIG. 6 is a graph of simulation results illustrating how a flat X-ray spectrum might be measured by a pixelated detector with no charge sharing and with 100% charge sharing.
Figure 9:
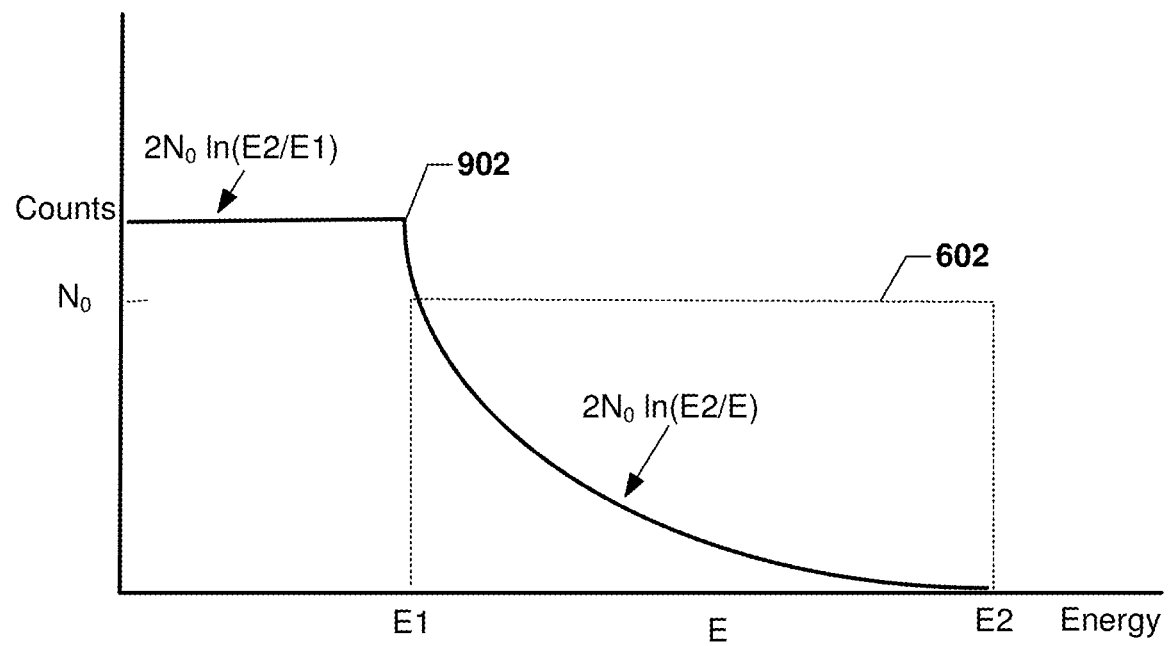
FIG. 9 is a graph illustrating a measured X-ray photon energy spectrum resulting from 100 percent (%) charge sharing of detected photons of an incident flat X-ray spectrum due to effects of charge sharing.

To calculate the detected energy spectrum under the effects of charge sharing, the spread of energies due to charge sharing for each photon energy increment E from energy 0 to E is determined and summed for all energies E across the incident energy spectrum (i.e., from E1 to E2). If the energy spectrum is defined by a formula, such as the flat energy spectrum 602 illustrated in FIGS. 6-8, then this calculation can be accomplished by integration. For example, for the flat energy spectrum 602 and the assumption of a flat spreading of photon energies due to 100% charge sharing, the detected energy spectrum, Y(E), due to charge sharing between E1 and E2 would be given by the integral from E2 to E of $2N_0$ dE/E, which is Y(E)=$2N_0$ ln(E2/E), while the detected energy spectrum due to charge sharing between zero and E1 would be the constant $2N_0$ ln(E2/E1) because all photons from E1 to E2 contribute to the counts. This calculated observed energy spectrum 902 due to 100% charge sharing is illustrated in FIG. 9.

Figure 10:
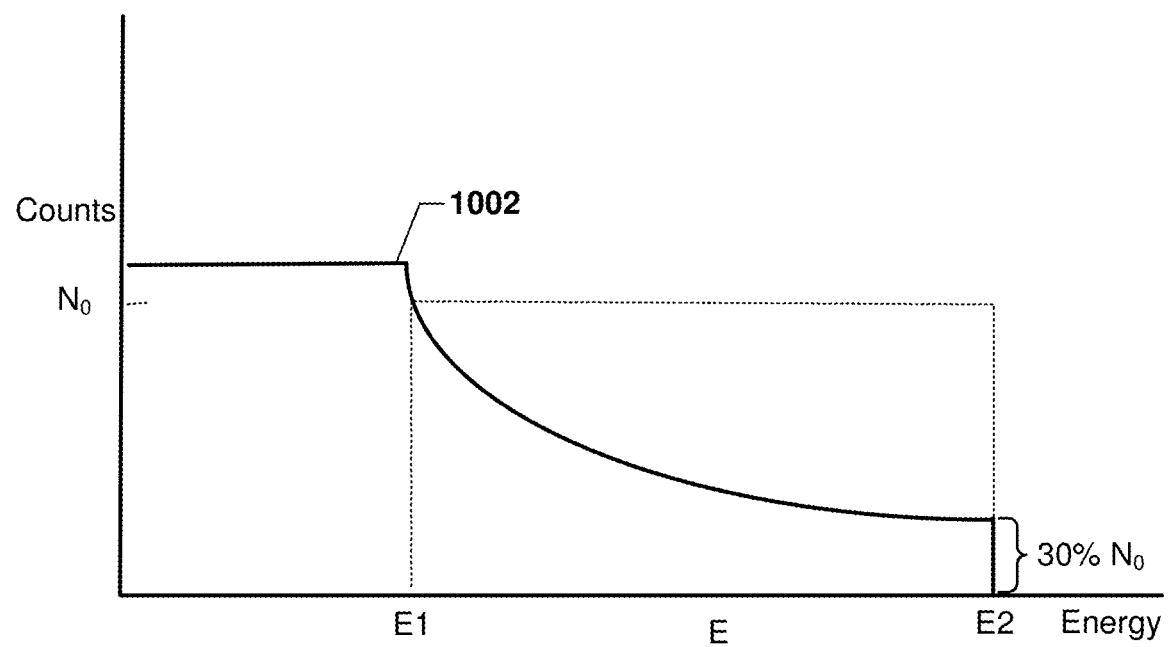
FIG. 10 is a graph illustrating a measured X-ray photon energy spectrum resulting from 70 percent (%) charge sharing of detected photons of an incident flat X-ray spectrum due to effects of charge sharing.

For the case in which not all photon interactions result in charge sharing among detector pixels, as when the area of pixel detectors is larger than the diameter of the electron cloud due to photon absorptions, then the detected energy spectrum would be the spectrum due to charge sharing times the fraction η of detections involving charge sharing plus the energy spectrum of the incident photons times the fraction (i–η) of photons detected without charge sharing. A notional measured X-ray photon energy spectrum 1002 resulting from 70% charge sharing (i.e., 30% of photon detections do not involve charge sharing) is illustrated in FIG. 10.

Figure 11:
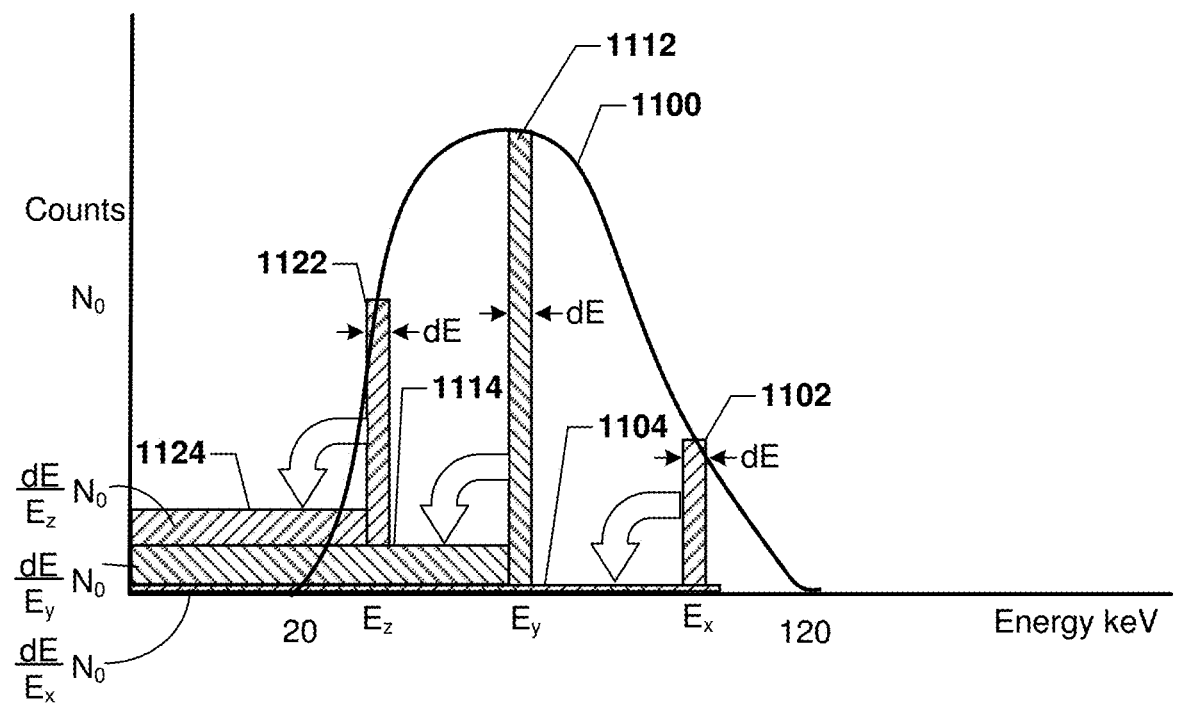
FIG. 11 is a graph illustrating how X-ray photon energies within multiple energy slices (dE) of a typical X-ray photon energy spectrum are spread across lower energies and add up to produce a measured X-ray photon energy spectrum that differs from the incident X-ray photon energy spectrum due to effects of charge sharing.
Figure 12:
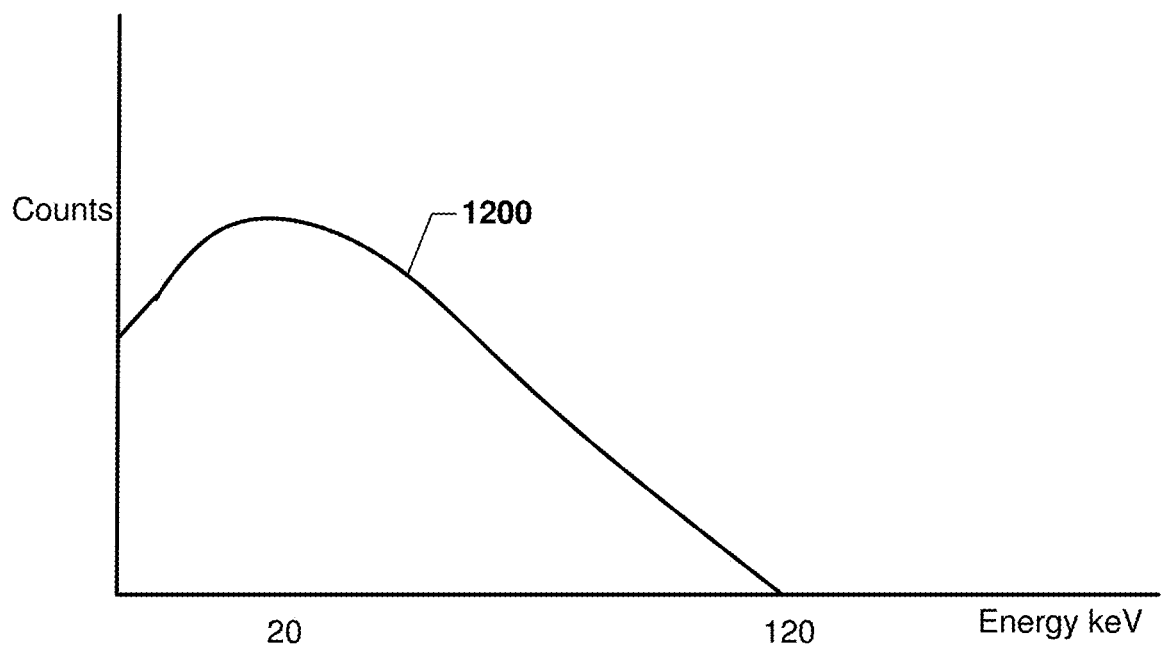
FIG. 12 is a graph illustrating an example of how the X-ray energy spectrum shown in FIG. 11 might be measured by a pixelated detector due to charge sharing effects.

For normal incident X-ray photon spectra are not characterized by a defined function, and thus not easily integrated mathematically. However, the detected energy spectrum with charge sharing may be estimated by determining the distribution of energy due to charge sharing of an increment of energies dE about an energy E, and summing the results for all dE's within the bounds of the incident spectrum. This is illustrated in FIG. 11, which shows how the number of photons within increments dE at energies $E_x$, $E_y$ and $E_z$ (illustrated in bars 1102, 1112 and 1122) between 20 keV and 120 keV are spread over the range between zero and $E_1$ (illustrated as layers 1104, 1114 and 1124, respectively), and added. This may be accomplished using any of a variety of know analysis tools, such as MATLAB, working with measurements, estimations or calculations of the incident photon energy spectrum. As illustrated notionally in FIG. 12, the result may be an observed energy spectrum that is shifted to lower energies with an increased total count of photons (since one photon may be counted in 2, 3 or 4 pixel detectors due to charge sharing).

Figure 13:
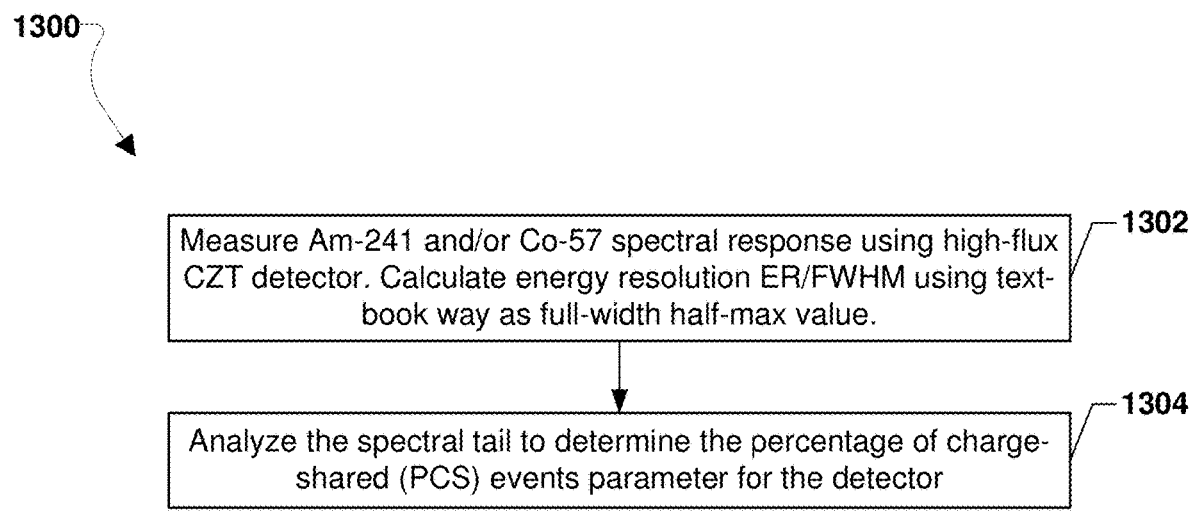
FIG. 13 is a process flow diagram illustrating a method of determining the energy resolution of a pixelated detector and the percentage of charge sharing that occurs in the pixelated detector according to some embodiments.

As the effects of charge sharing depend upon the percentage of photon events that experience charge sharing, the percentage of charge sharing (PCS) characteristic parameter of a detector may be determined in a first set of operations. FIG. 13 illustrates a method 1300 that may be used to determine the energy resolution (ER) and PCS parameters for a given detector. The method 1300 may be performed as part of a calibration process of a manufactured detector, or may be performed to determine the PCS parameter of a detector design.

In operation 1302, the X-ray spectrum of an isotope with a specific or narrow energy X-ray emission, such as Am-241 and or Co-57, may be measured by the detector. Using the textbook methods, the energy resolution (ER) of the detector may be determined such as by using the full-width half-max value (FWHM) of the peak in the measured energy spectrum as a measure of the energy resolution. X-rays emitted at the specific energy X-ray emission exhibit a narrow range of energies (broadened due to thermal and quantum effects). Thus, if the detector exhibited very high energy resolution, the detector would record a very narrow range of energies centered about the specific energy of the X-ray emission. The finite energy resolution of detectors may be due to several factors, but the net result is a broadening of the measured energies about the specific energy of the X-ray emission. Thus in operation 1302, a measure of the energy resolution of the detector may be made by determining the width or range of photon energies recorded by the detector at a count-rate in the measure photon energy spectrum that is half way between zero and the maximum counts at or near the specific energy of the X-ray emissions of the isotope.

In operation 1304, the measured spectrum may be analyzed to measure the spectral tail below the peak emission(s) to determine the percentage of charge sharing events occurring in the detector. By using an isotope with a narrow X-ray emission, the effects of charge sharing are obvious in the detected energy spectrum below the isotope's X-ray energy peak, particularly within the measured spectrum that is less than the energy of the isotope's characteristic X-ray plus half of the energy resolution of the detector determined in operation 1302. The percentage of charge sharing events may be determined as a ration of the measured total energy in the spectral tail to the total energy measured (i.e., spectral tail plus peak emission). Said another way, the percentage of charge sharing parameter of the pixelated detector may be determined by using the pixelated detector to measure X-ray photon energies emitted by an isotope with a specific energy X-ray emission, such as Am-241 and or Co-57, and determining the fraction of photon detection counts with energies less than the specific energy X-ray emission plus half of the energy resolution to all photon detection counts including counts about the specific energy of the characteristic X-ray emission of the isotope.

Figure 14:
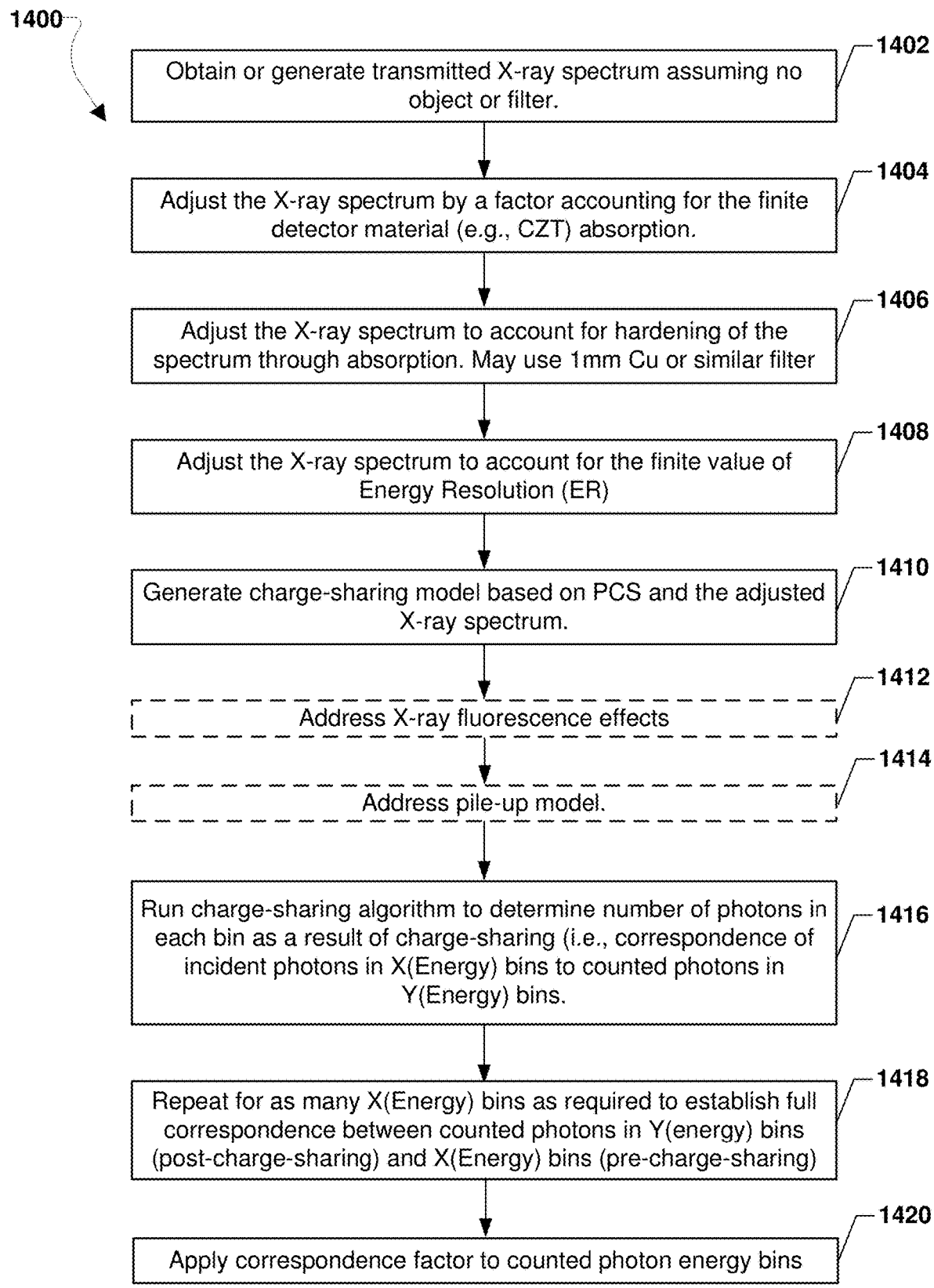
FIG. 14 is a process flow diagram illustrating a method of compensating for charge sharing as well as other phenomena affecting a measure X-ray energy spectrum recorded by a pixelated detector according to some embodiments.
Figure 15:
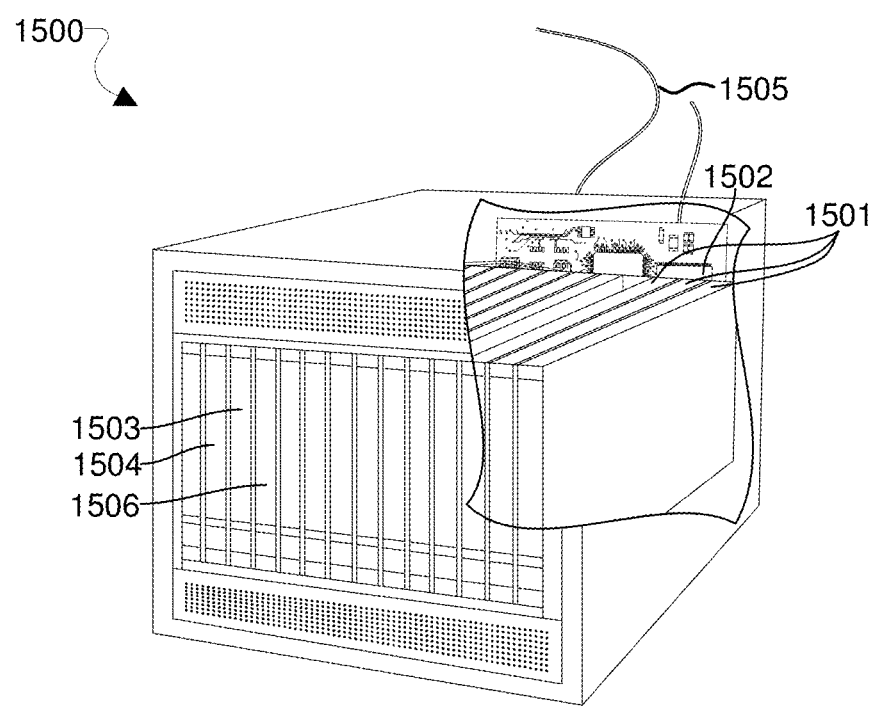
FIG. 15 is a component block diagram illustrating an example server suitable for use with the various embodiments.

The energy resolution and percentage of charge sharing events determined in the method 1300 may then be used as inputs to the method 1400 illustrated in FIG. 14 for correlating detected X-ray photon energies to an emitted X-ray photon spectrum and select a number of energy bins to use or a particular application, such as nondestructive testing.

The method 1400 may be implemented in a computing device as part of and imaging system design process, as part of a calibration process, and/or as part of configuring X-ray imaging nondestructive test equipment for particular application.

To relate the observed X-ray energy spectrum to the energy spectrum of X-ray photons emitted from the X-ray tube, all of the mechanisms affecting the detection of photons by the pixelated detector may be taken into account in the method 1400 before determining the effects of charge sharing.

In block 1402, the X-ray photon spectrum admitted from an X-ray tube may be obtained or determined, such as by simulation using a variety of available tools. An example of such a tool is a Siemens online simulation tool for determining the X-ray spectrum from an X-ray tube as a function of voltage and current, although other simulation tools may be used. (See https://www.oem-products.siemens-healthineers.com/X-ray-spectra-simulation). This simulation may use input the kVpp of the X-ray tube and the target material (Tungsten, Molybdenum, etc.). In some embodiments, a low mA current (typically 1 mA for 30 cm tube to detector distance) may be assumed to ensure that the X-ray flux remains in non-pile-up regime. In some embodiments, a table look up of the X-ray spectrum of a given X-ray tube at a given power level may be used.

In block 1404, the X-ray photon spectrum may be adjusted by addressing the finite absorption characteristics of the detector material (e.g., CZT). For example, an efficiency or similar factor may be applied to the spectrum determined in block 1402. The probability of a photon being absorbed in a particular detector depends upon the energy of the photon, the thickness of the detector, and the atoms making up the detector material. Detector materials including high Z atoms, such as cesium and tungsten (e.g., in CZT detectors) tend to have a high probability of interacting with an X-ray photon. A database available from the National Institute of Science and Technology (NIST) or equivalent may be used in this calculation. Alternatively, MATLAB or equivalent code may be used to estimate the detector absorption factor. The detector absorption factor determined in operation 1404 may be used to account for the fact that X-ray photons that are not absorbed in the detector go uncounted, and thus represent a fraction of the spectrum that will not be measured.

In operation 1406, the X-ray photon spectrum may be adjusted to account for the X-ray hardening effects of a filter and/or an object under examination. As an example, a 1 mm thick copper sheet (or similar material) placed in the X-ray beam (or assumed in simulations) to determine or approximate the hardening of the X-ray spectrum that will be caused by preferential absorption of lower energy X-rays within the filter and/or material subject to the nondestructive testing. Online tools (e.g., the Siemens tool) may be used to simulate a revised X-ray photon spectrum due to the filter effect based upon the particular filter material (e.g., copper, aluminum, etc.) and the thickness of the filter. Alternatively, physical measurements of the X-ray spectrum may be made with the imaging system with and without a filter positioned in the X-ray beam.

In block 1408, the X-ray photon spectrum may be adjusted to account for the effects of the energy resolution (ER) determined in operation 1302 of the method 1300 may be added. As discussed above, the energy resolution factor accounts for the inherent error in the measurement made by the detector of a given photon's energy due to a variety of effects inherent in the detector materials and the detector design. The exact value of energy resolution is not critical (e.g., such as not determined using the method 1300) as long as it is ballpark correct (+/−2 keV) to smooth sharp transitions that might interfere with bin assignments.

In block 1410, a charge sharing model based on the PCS value determined in block 1304 of the method 1300 may be used to determine (e.g., via calculations discussed above) how the revised X-ray spectrum is shifted to greater counts at lower energies due to charge sharing based on the PCS parameter by using the calculational methods described above with reference to FIGS. 11 and 12. Knowing the PCS parameter, tools such as MATLAB can be used to simulate of the X-ray spectrum will be measured by the pixelated detector due to charge sharing by incrementally shifting (smearing) the fraction of photons in each narrow slice dE of the revised energy spectrum and summing the results to obtain an anticipated measured energy spectrum (e.g., illustrated in FIG. 12).

In optional operation 1412, the effects of X-ray fluorescence may be added to the anticipated measured energy spectrum. As discussed above, X-ray fluorescence is generally not of significance unless the nondestructive testing makes use of X-rays with energies less than about 35 keV. If the application uses X-rays harder than this value, optional block 1312 may not be implemented. Alternatively, the effects of X-ray fluorescence may be treated as part of the anticipated measured energy spectrum.

In optional operation 1414, the effects of pileup detections may be added to the anticipated measured energy spectrum. This operation is optional because in low flux testing applications, the probability of pileup detections is small enough to be ignored.

In operation 1416, a number (and thus energy bands) of energy bins to be used in measuring the detected photon energies may be selected, and the anticipated measured energy spectrum may be allocated to the selected energy bins to determine the number of photons that may be counted in each energy bin after the effects of hardening, energy resolution and charge sharing. The resulting energy bin picture of the spectrum may be compared to the anticipated measured energy spectrum to determine the correspondence of the incident photons in the selected energy bins to the number of photons that can be expected to be counted in each of the selected energy bins.

In operation 1418, a different number of energy bins may be selected and the operations of block 1416 may be repeated, with the results compared until a selection of energy bins is achieved that establishes full correspondence between the observed photon energy spectrum after charge sharing and the incident photon energy spectrum (i.e., before charge sharing).

In operation 1420, the correspondence between the observed photon energy spectrum after charge sharing ("post-charge-sharing") and the incident photon energy spectrum ("pre-charge-sharing") determined in blocks 1416 and 1418 may be used as correction factors for estimating the actual spectrum of the incident X-rays in energy bins based on the actual energy bin counts as determined by the detector. For example, the correspondence factor may be determined by comparing the estimated counts in each of the energy bins determined in blocks 1416 and 1418 to counts in the energy bins that would be expected for the adjusting the incident X-ray photon energy spectrum determined in block 1408. In this manner, the effects of charge-sharing on energy bin distributions of detected X-ray photons may be backed out or accounted for via a simple mathematical adjustment. This may provide satisfactory adjustments for charge sharing without the need for detecting charge sharing events and summing measured energies into a single pixel detector selected as the site of detection (e.g., described with reference to FIGS. 4A and 4B).

Various embodiments (including, but not limited to, the embodiment methods described above with reference to FIGS. 12-15) may be implemented in computing systems, such as any of a variety of commercially available computers 1600 as illustrated in FIG. 16. Such a computer 1600 typically includes one or more processors 1601 coupled to volatile memory 1602 and a large capacity nonvolatile memory, such as a disk drive 1604. As illustrated in FIG. 16, one or more processors 1601 may be added to the computer 1600 by inserting them into the racks of the assembly. The computer 1600 may also include a floppy disc drive, compact disc (CD) or digital versatile disc (DVD) disc drive 1606 coupled to the one or more processors 1601. The computer 1600 may also include network access ports 1603 coupled to the one or more processors 1601 for establishing network interface connections with a network 1605, such as a local area network coupled to other computers and servers, or the Internet.

The present embodiments may be implemented in systems used for medical imaging, such as X-ray imaging, as well as for non-medical imaging applications, such as industrial inspection applications.

Computer program code or executable instructions for execution on a programmable processor for carrying out operations of the various embodiments may be written in a high level programming language such as C, C++, C #, Smalltalk, Java, JavaScript, Visual Basic, a Structured Query Language (e.g., Transact-SQL), Perl, or in various other programming languages. Embodiments may be implemented as program code or processor-executable instructions stored on a non-transitory processor-readable storage medium that are configured to cause a processor coupled to a pixelated radiation detector, such as a processor or analysis unit of an X-ray imaging system, to perform operations of any of the various embodiments. Program code or processor-executable instructions stored on a non-transitory processor readable storage medium as used in this application may refer to machine language code (such as object code) whose format is understandable by a processor. Non-transitory processor-readable storage medium include any form of media used for storing program code or processor-executable instructions including, for example, RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a processor or computer.

While the disclosure has been described in terms of specific embodiments, it is evident in view of the foregoing description that numerous alternatives, modifications and variations will be apparent to those skilled in the art. Each of the embodiments described herein may be implemented individually or in combination with any other embodiment unless expressly stated otherwise or clearly incompatible. Accordingly, the disclosure is intended to encompass all such alternatives, modifications and variations which fall within the scope and spirit of the disclosure and the following claims.

What is claimed is:

1. A method of accounting for difference between observed energies X-ray photons and an incident X-ray photon energy spectrum that accounts for charge sharing in a pixelated detector within an X-ray imaging system, the method comprising:
   applying a correspondence factor to counts of X-ray photons in energy bins to estimate incident X-ray photon energy bins, wherein the correspondence factor accounts for charge sharing within the pixelated detector; and
   further comprising determining the correspondence factor by performing operations comprising:
      determining a photon energy spectrum of X-ray photons incident on the pixelated detector which comprises the incident X-ray photon energy spectrum;
      adjusting the incident X-ray photon energy spectrum to account for an energy resolution of the pixelated detector;
      generating a charge sharing model for the adjusted incident X-ray photon energy spectrum based on a percentage charge sharing parameter of the pixelated detector, the charge sharing model accounting for shifts in photon energies and detections occurring in photon detections due to charge sharing in the pixelated detector;
      applying the charge sharing model to energy bins of the pixelated detector to estimate counts in each of the energy bins; and
      determining the correspondence factor by comparing the estimated counts in each of the energy bins to counts in the energy bins that would be expected for the adjusting the incident X-ray photon energy spectrum.

2. The method of claim 1, wherein determining the incident X-ray photon energy spectrum comprises:
   obtaining an X-ray photon energy spectrum emitted from an X-ray tube of the imaging system;
   adjusting the emitted X-ray photon energy spectrum by a factor accounting for X-ray photon absorption properties of the pixelated detector; and
   further adjusting the X-ray photon energy spectrum to account for hardening of the spectrum due to effects of one or both of a filter in the X-ray imaging system or of an object under examination in the X-ray imaging system.

3. The method of claim 1, further comprising determining the energy resolution of the pixelated detector by measuring, with the pixelated detector, X-ray photon energies emitted by an isotope with a characteristic X-ray emission of a specific energy, and determining a range of measured energies having at least a count rate equal to half of a maximum count rate at a measured energy peak corresponding to the specific energy of the characteristic X-ray emission of the isotope.

4. The method of claim 3, further comprising determining the percentage of charge sharing parameter of the pixelated detector by measuring, with the pixelated detector, X-ray photon energies emitted by an isotope with a specific energy X-ray emission and determining a fraction of photon detection counts with energies less than the specific energy X-ray emission plus half of the energy resolution to all photon detection counts including counts about the specific energy of the isotope characteristic X-ray emission.

5. The method of claim 1, further comprising adjusting the charge sharing model to address X-ray fluorescence effects.

6. The method of claim 1, further comprising adjusting the charge sharing model to address pile-up effects.

7. The method of claim 1, further comprising:
   selecting a number of energy bins; and
   repeating operations of applying the charge sharing model to the selected energy bins and determining the correspondence factor until a full correspondence is established between counted photons in the selected energy bins and counts in the energy bins that would be expected for the adjusting the incident X-ray photon energy spectrum.

8. The method of claim 1, wherein generating a charge sharing model for the adjusted incident X-ray photon energy spectrum based on a percentage charge sharing parameter of the pixelated detector comprises:
    for the full the adjusted incident X-ray photon energy spectrum, spreading count rates of narrow slices of the adjusted incident X-ray photon spectrum across energies from zero to the energy of each narrow slice; and
    summing all spread count rates to determine an X-ray photon energy spectrum that would be observed by the pixelated detector due to charge sharing before segmenting the spectrum into energy bins.

9. An imaging X-ray detector comprising a plurality of pixel detectors and means for performing functions of the method of claim 1.

10. Circuitry for use with an X-ray detector comprising a plurality of pixel detectors and configured to perform functions of the method of claim 1.

\* \* \* \* \*